(12) United States Patent
Clark

(10) Patent No.: US 10,179,128 B2
(45) Date of Patent: Jan. 15, 2019

(54) REGIMENS FOR TREATING AND PREVENTING LYSOSOMAL DISORDERS AND DEGENERATIVE DISORDERS OF THE CENTRAL NERVOUS SYSTEM

(71) Applicant: Amicus Therapeutics, Inc., Cranbury, NJ (US)

(72) Inventor: Sean Clark, Montgomery, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 15/251,559

(22) Filed: Aug. 30, 2016

(65) Prior Publication Data

US 2017/0056384 A1 Mar. 2, 2017

Related U.S. Application Data

(60) Provisional application No. 62/212,291, filed on Aug. 31, 2015.

(51) Int. Cl.
*A61K 31/445* (2006.01)
*A61K 9/00* (2006.01)

(52) U.S. Cl.
CPC .......... *A61K 31/445* (2013.01); *A61K 9/0053* (2013.01)

(58) Field of Classification Search
None
See application file for complete search history.

(56) References Cited

U.S. PATENT DOCUMENTS

| 8,604,057 B2 * | 12/2013 | Boyd .................. A61K 31/445 |
| | | 514/315 |
| 9,056,101 B2 * | 6/2015 | Lockhart ............. A61K 31/445 |
| 2011/0091442 A1 | 4/2011 | Boyd et al. |
| 2011/0092541 A1 | 4/2011 | Boyd et al. |
| 2015/0050263 A1 | 2/2015 | Boyd |

FOREIGN PATENT DOCUMENTS

| WO | 2008134628 A2 | 11/2008 |
| WO | 2011049787 A1 | 4/2011 |
| WO | 2013148103 A1 | 10/2013 |

OTHER PUBLICATIONS

Berge, S et al J. Pharm Sci 1977 vol. 66 pp. 1-19.*
Rolfs, A. et al., PLOS ONE 2013 vol. 8 issue 11 pp. 1-9.*
Dandana, A. et al., Pathobiol. 2013 pp. 13-23.*
Sanders, et al., "Transgenic mice expressing human glucocerebrosidase variants: Utility for the study of Gaucher disease", Blood Cells Mol. Diseases (2013), (http://dx.doi.org/10.1016/j.bcmd.2013.03.006), 8 pages.
Jang-Woo, Shin, et al., "Interpretation of Animal Dose and Human Equivalent Dose for Drug Development", The Journal of Korean Medicine (2010), vol. 31, No. 3, pp. 1-7.
PCT International Search Report and Written Opinion in PCT/US2016/049614 dated Nov. 8, 2016, 18 pages.

* cited by examiner

*Primary Examiner* — Heidi Reese
(74) *Attorney, Agent, or Firm* — Servilla Whitney LLC

(57) ABSTRACT

Described herein are dosing regimens and kits for the treatment and/or prevention of lysosomal storage disorders such as Gaucher disease. Also described are dosing regimens and kits for the treatment and/or prevention of degenerative disorders of the central nervous system, such as the synucleinopathies Parkinson's disease or Lewy Body Dementia.

18 Claims, 24 Drawing Sheets

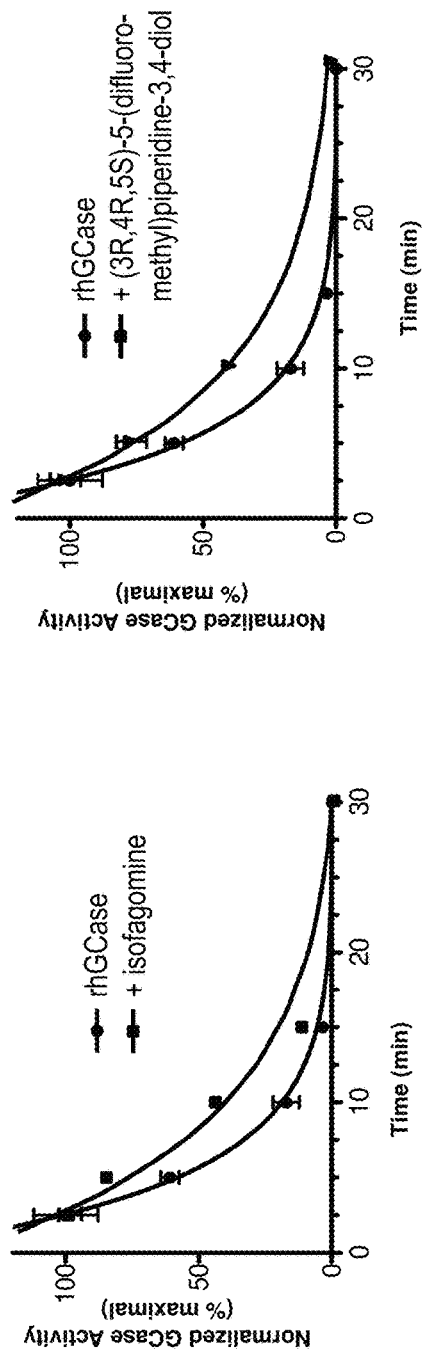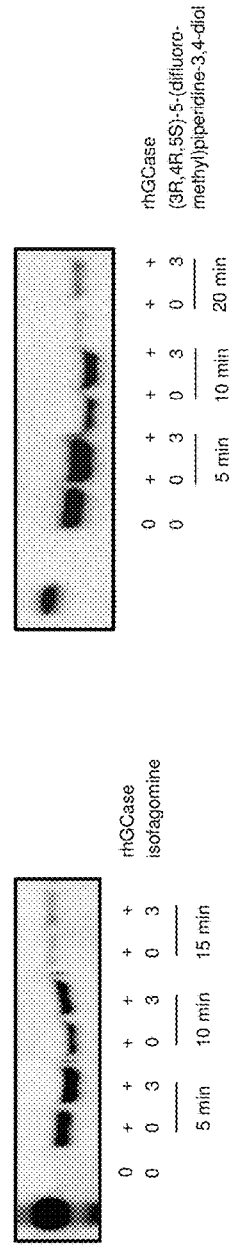
FIG. 3A
FIG. 3B
FIG. 3C
FIG. 3D

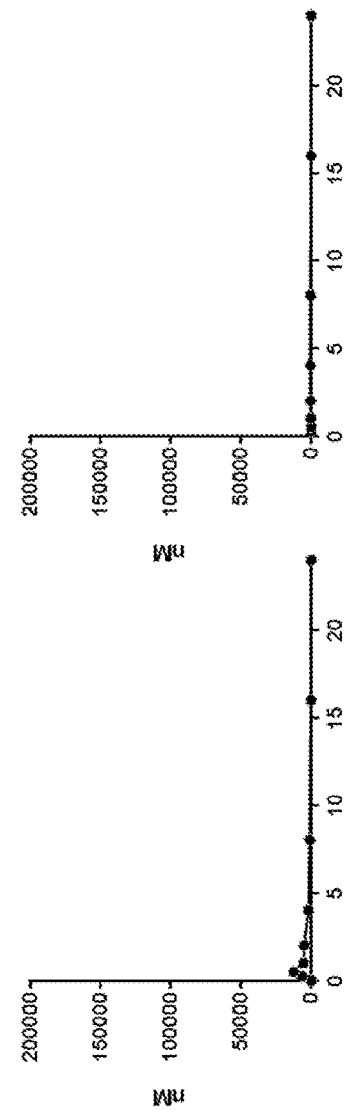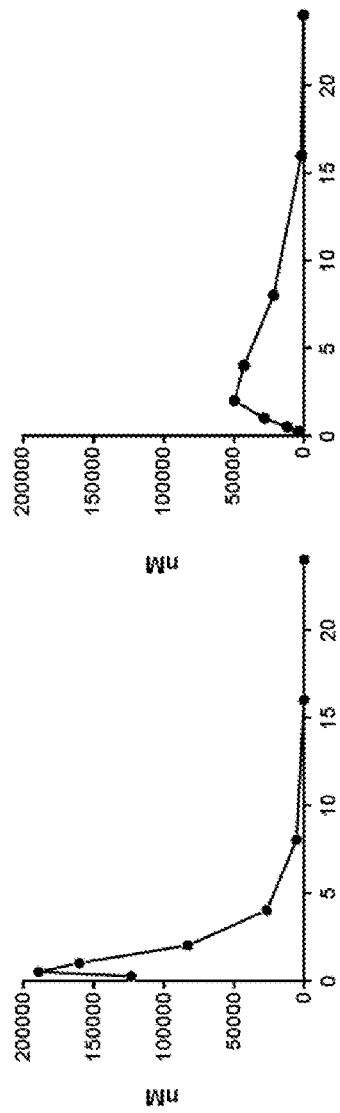
FIG. 6A, FIG. 6B, FIG. 6C, FIG. 6D

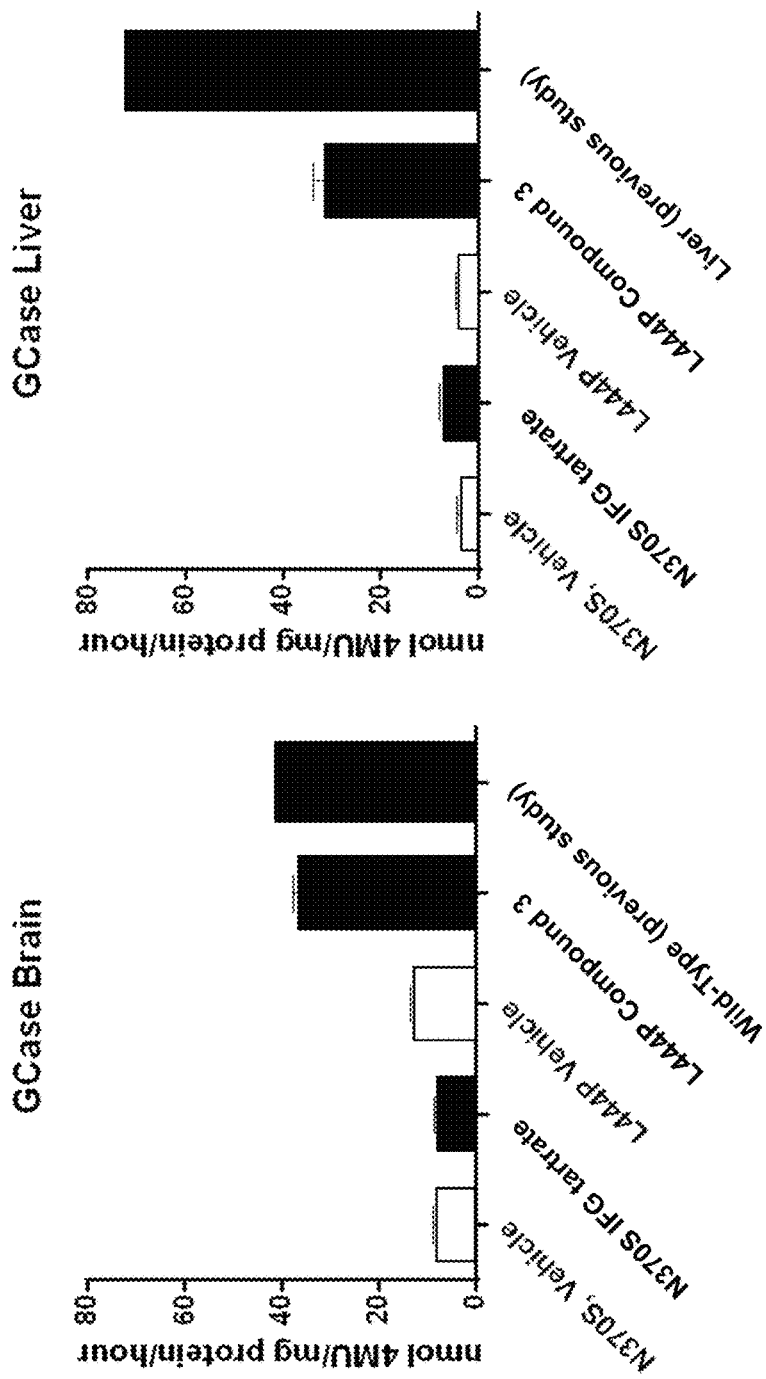

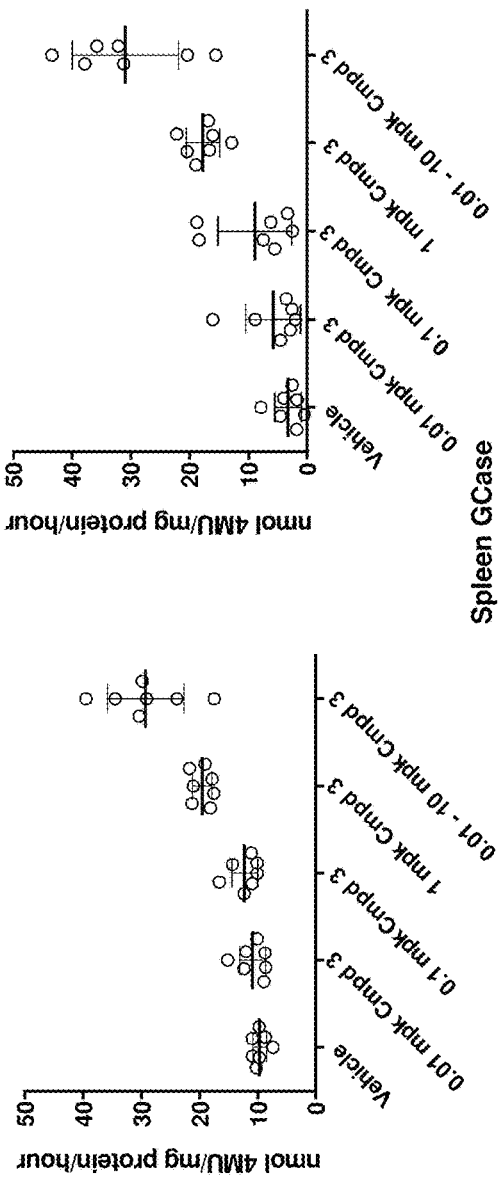
FIG. 11A
FIG. 11B
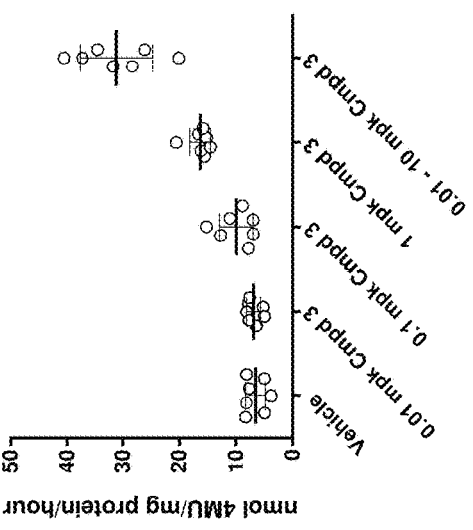
FIG. 11C

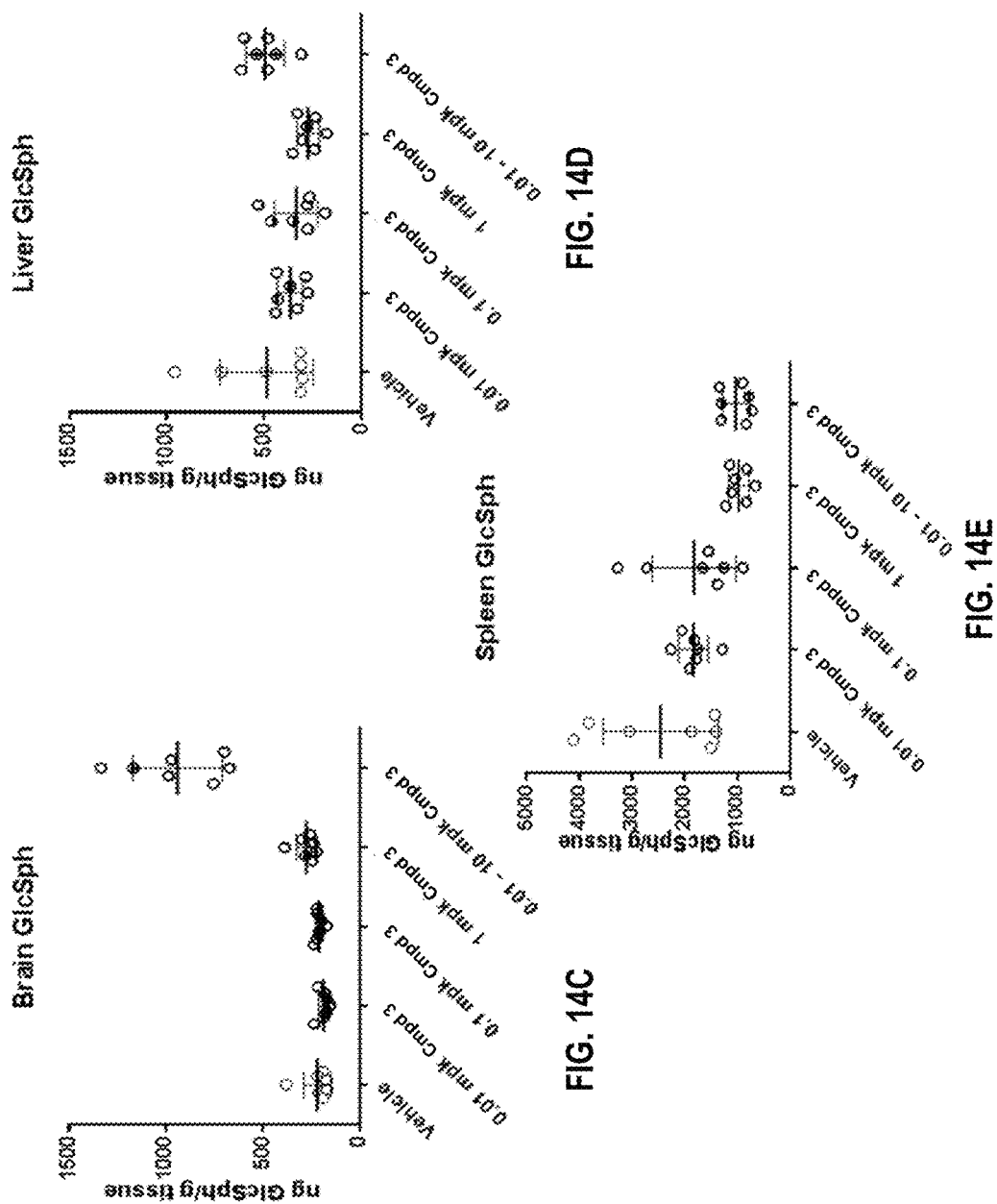

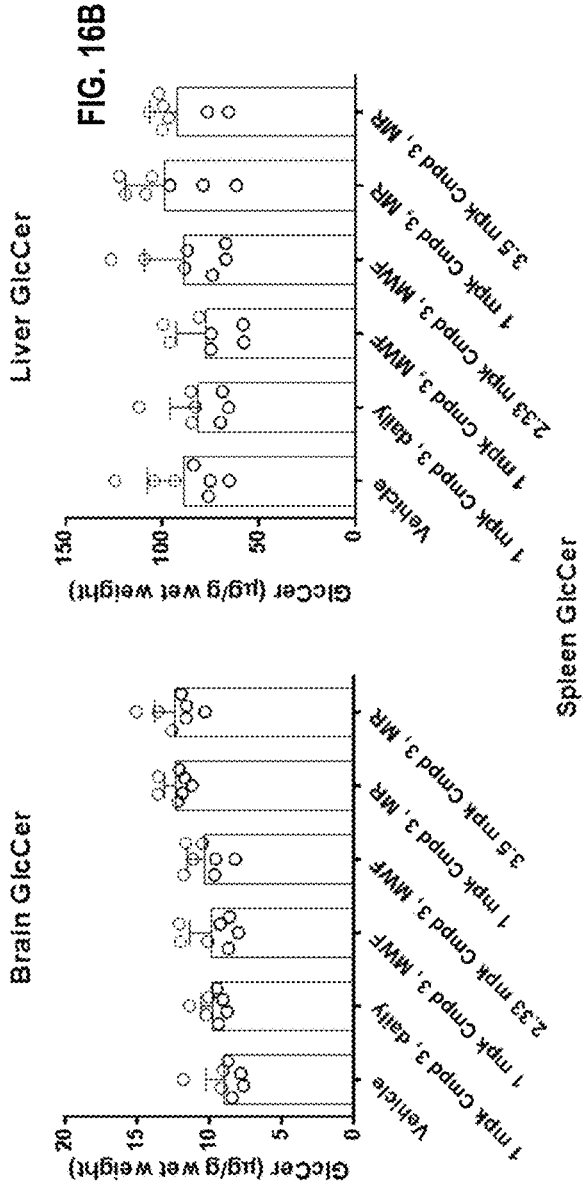
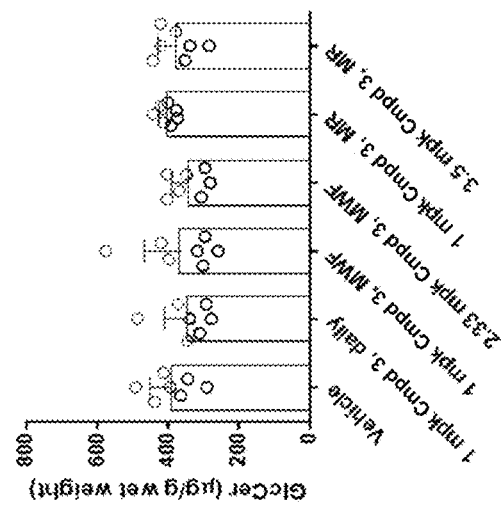

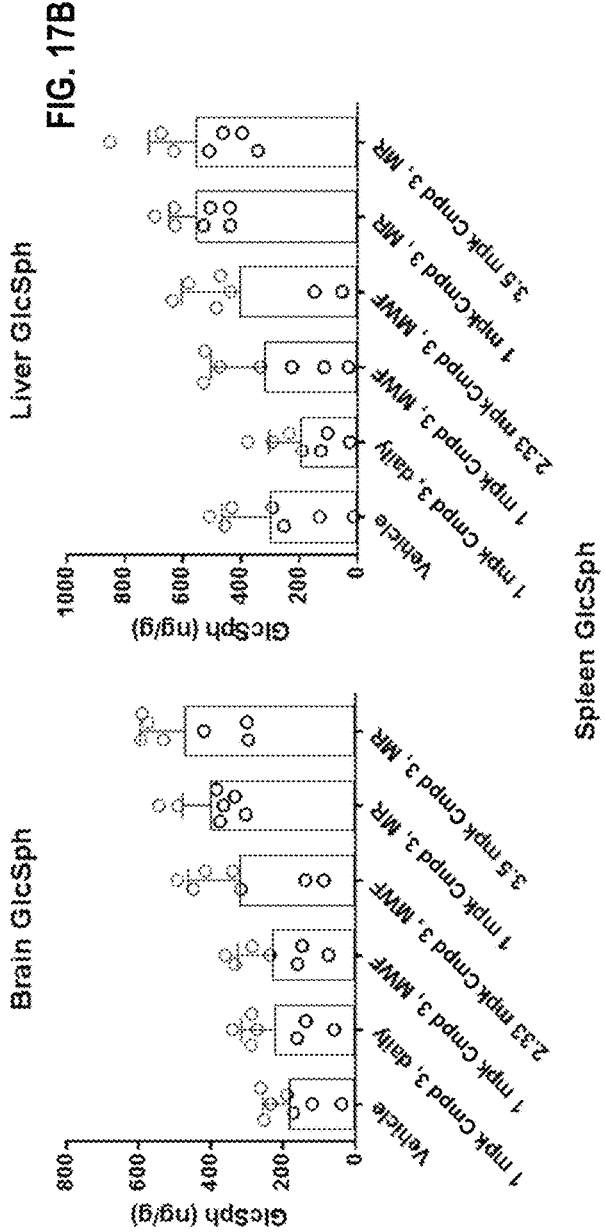

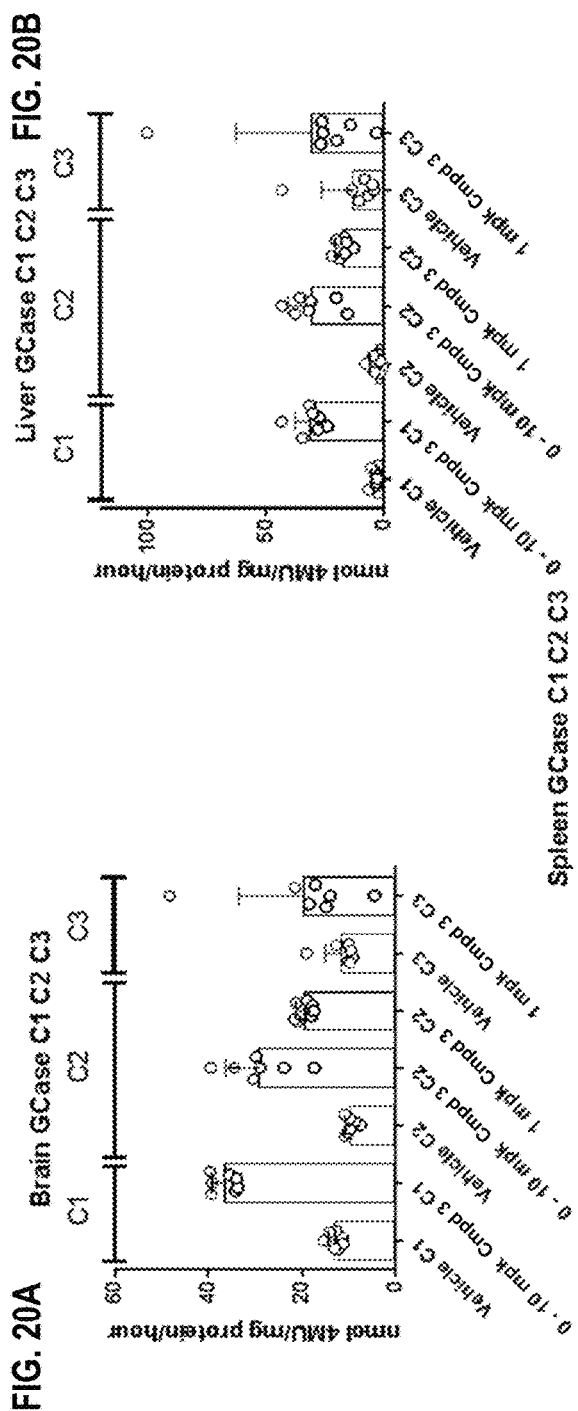
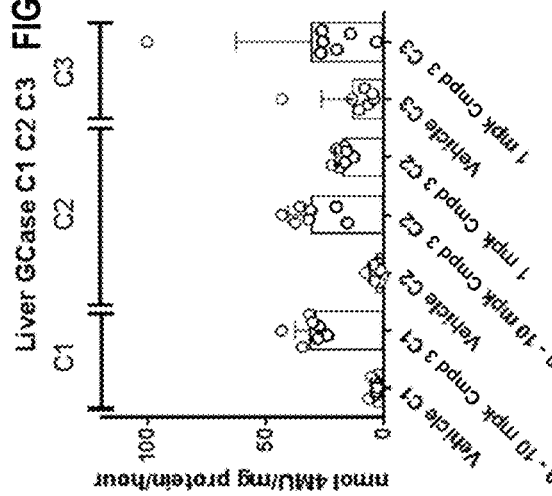
FIG. 20A
FIG. 20B
FIG. 20C

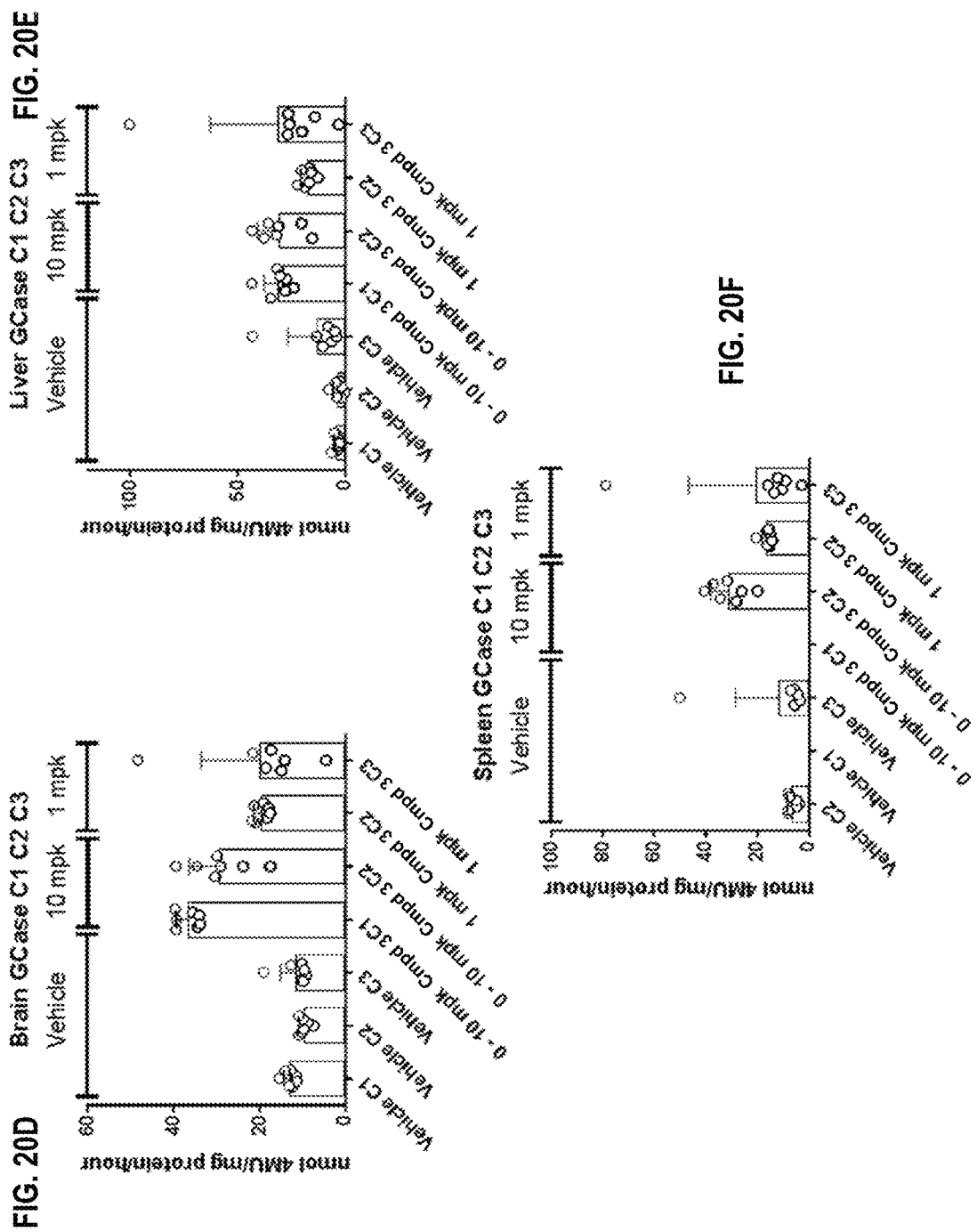

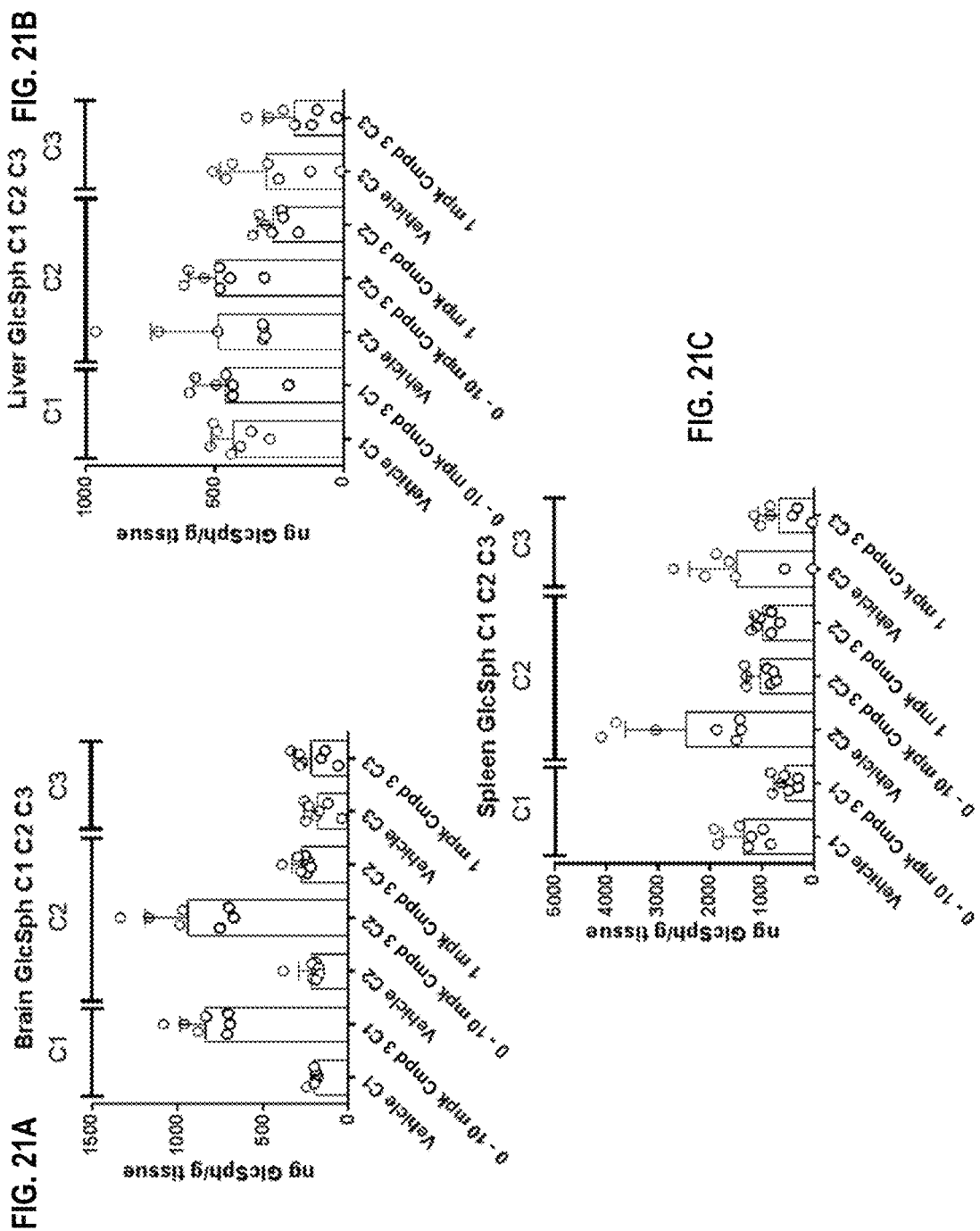

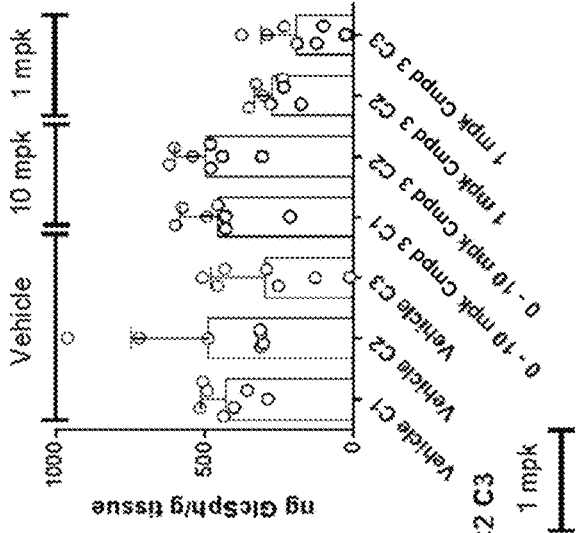
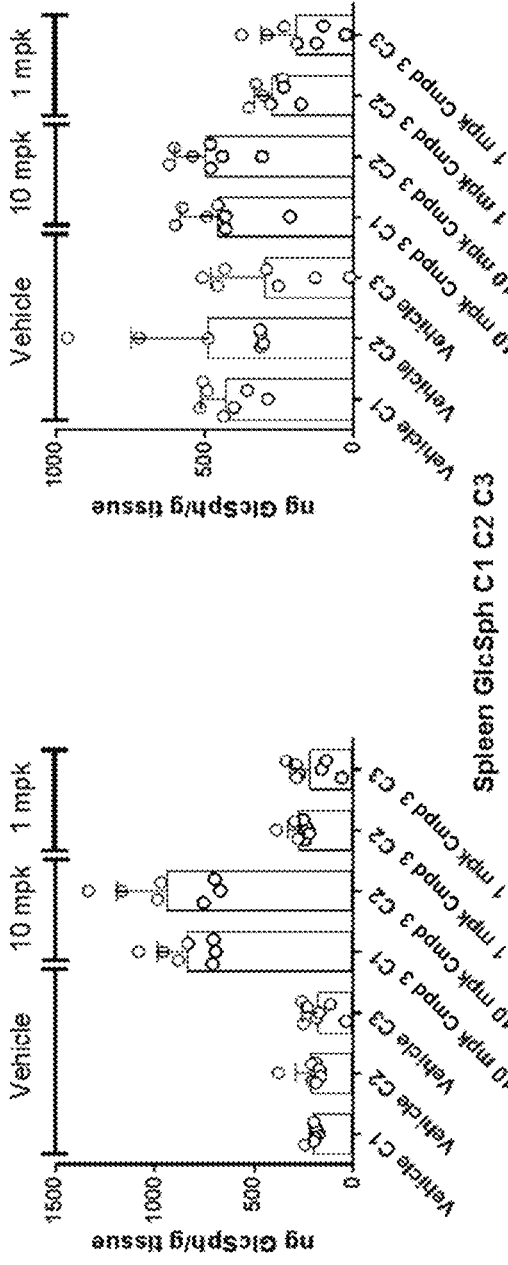
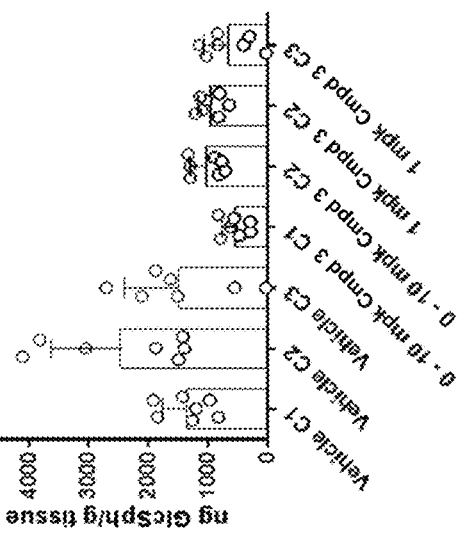

REGIMENS FOR TREATING AND PREVENTING LYSOSOMAL DISORDERS AND DEGENERATIVE DISORDERS OF THE CENTRAL NERVOUS SYSTEM

CROSS-REFERENCE TO RELATED APPLICATIONS

This application claims the benefit under 35 U.S.C. § 119(e) to U.S. Provisional Application No. 62/212,291, filed Aug. 31, 2015, the entire contents of which are incorporated herein by reference in their entirety.

TECHNICAL FIELD

The present invention generally pertains to the prevention and/or treatment of lysosomal disorders and/or degenerative disorders of the central nervous system using pharmacological chaperones.

BACKGROUND

Lysosomal storage disorders are caused by a defect in lysosomal function that results in accumulation of substances within the lysosome of cells. This defect is usually a consequence of deficiency of a single enzyme required for the metabolism of lipid, glycogen, glycoprotein, or mucopolysaccharide. Gaucher disease, the most common lysosomal storage disorder, is caused by a deficiency in β-glucocerebrosidase (also known as beta-glucosidase or GCase).

Gaucher disease is an autosomal recessive disorder caused by mutations in the GBA gene, which encodes for GCase. This enzyme functions inside the acidic environment of the lysosome and reacts with two key substrates: glucocerebroside (GlcCer) and Glucosylsphingosine (GlcSph). Mutations in the GBA gene lead to a partial or total loss of function phenotype, and can be characterized by reduced or absent GCase activity in the lysosome, and accumulation of GCase substrate, leading to a variety of symptoms.

Gaucher disease is categorized into three types. Approximately 95% of patients with Gaucher exhibit Type 1, where onset occurs at childhood or adulthood and has been described as non-neuronopathic. Type 2 is characterized by the presence of neurologic involvement during childhood, whereas neurologic involvement presents during adolescence or adulthood in Type 3 Gaucher disease.

Parkinson's disease is an adult neurodegenerative disorder that is characterized by a progressive loss of motor and other neural functions. The disease can be identified pathologically by two primary features: neuronal death and Lewy bodies. As the disease progresses, the neurons in the brain that control movement begin to die and the hallmark clinical signs of Parkinson's begin to appear, including tremors, stiffness, and difficulty with posture. Within the remaining surviving neurons, proteins and lipids begin to accumulate into bodies known as Lewy bodies. One key component identified within Lewy bodies is alpha-synuclein, and variations in its gene, SNCA, are associated with inherited and sporadic Parkinson's.

Accordingly, there is a need for additional treatments for lysosomal storage disorders such as Gaucher disease and degenerative disorders of the central nervous system such as Parkinson's disease.

SUMMARY

One aspect of the present invention is directed to a method for preventing and/or treating a synucleinopathy in a patient at risk for developing or diagnosed with the same, the method comprising: administering to the patient an effective amount of (3R,4R,5S)-5-(difluoromethyl) piperidine-3,4-diol or a salt thereof for a first enzyme enhancement period; not administering the (3R,4R,5S)-5-(difluoromethyl) piperidine-3,4-diol or salt thereof for a substrate turnover period; and then administering to the patient an effective amount of (3R,4R,5S)-5-(difluoromethyl) piperidine-3,4-diol or a salt thereof for a second enzyme enhancement period.

In one or more embodiments of this aspect, the effective amount is in the range of about 50 to about 300 mg free base equivalent (FBE) per day. In some embodiments, the patient is administered about 300 to about 700 mg FBE per week. In some embodiments, the effective amount is in the range of about 0.75 to about 1.5 mg/kg/day FBE.

In exemplary embodiments, administering for a first enzyme enhancement period, not administering for a substrate turnover period, and administering for a second enzyme enhancement period comprises:
 a. administering about 50 to about 100 mg FBE per day for 7 days a week;
 b. administering about 50 to about 100 mg FBE per day for 3 days a week;
 c. administering about 50 to about 100 mg FBE per day for 2 days a week;
 d. administering about 100 to about 200 mg FBE per day for 3 days a week; or
 e. administering about 200 to about 300 mg FBE per day for 2 days a week.

According to one or more embodiments, the first enzyme enhancement period and the second enzyme enhancement period have the same duration.

In one or more embodiments, the (3R,4R,5S)-5-(difluoromethyl) piperidine-3,4-diol or salt thereof is administered about 2 to about 3 days a week. In other embodiments, the (3R,4R,5S)-5-(difluoromethyl) piperidine-3,4-diol or salt thereof is administered 7 days a week.

In some embodiments, the (3R,4R,5S)-5-(difluoromethyl) piperidine-3,4-diol or salt thereof is administered orally.

In some embodiments, the salt is (3R,4R,5S)-5-(difluoromethyl)piperidine-3,4-diol fumarate.

In one or more embodiments, the synucleinopathy is selected from Parkinson's disease and Lewy Body Dementia.

Another aspect of the present invention is directed to a method for preventing and/or treating Gaucher disease in a patient at risk for developing or diagnosed with the same, the method comprising: administering to the patient an effective amount of (3R,4R,5S)-5-(difluoromethyl) piperidine-3,4-diol or a salt thereof for a first enzyme enhancement period; not administering the (3R,4R,5S)-5-(difluoromethyl) piperidine-3,4-diol or salt thereof for a substrate turnover period; and then administering to the patient an effective amount of (3R,4R,5S)-5-(difluoromethyl) piperidine-3,4-diol or a salt thereof for a second enzyme enhancement period.

In one or more embodiments of this aspect, the effective amount is in the range of about 50 to about 300 mg free base equivalent (FBE) per day. In some embodiments, the patient is administered about 300 to about 700 mg FBE per week. In some embodiments, the effective amount is in the range of about 0.75 to about 1.5 mg/kg/day FBE.

In exemplary embodiments, administering for a first enzyme enhancement period, not administering for a substrate turnover period, and administering for a second enzyme enhancement period comprises:
 a. administering about 50 to about 100 mg FBE per day for 7 days a week;

b. administering about 50 to about 100 mg FBE per day for 3 days a week;

c. administering about 50 to about 100 mg FBE per day for 2 days a week;

d. administering about 100 to about 200 mg FBE per day for 3 days a week; or e. administering about 200 to about 300 mg FBE per day for 2 days a week.

According to one or more embodiments, the first enzyme enhancement period and the second enzyme enhancement period have the same duration.

In one or more embodiments, the (3R,4R,5S)-5-(difluoromethyl) piperidine-3,4-diol or salt thereof is administered about 2 to about 3 days a week. In other embodiments, the (3R,4R,5S)-5-(difluoromethyl) piperidine-3,4-diol or salt thereof is administered 7 days a week.

In some embodiments, the (3R,4R,5S)-5-(difluoromethyl) piperidine-3,4-diol or salt thereof is administered orally.

In some embodiments, the salt is (3R,4R,5S)-5-(difluoromethyl)piperidine-3,4-diol fumarate.

BRIEF DESCRIPTION OF THE DRAWINGS

FIGS. 3A-3D show the half-life of active rhGCase in rats after oral administration of a salt of isofagomine and a salt of (3R,4R,5S)-5-(difluoromethyl)piperidine-3,4-diol;

FIGS. 6A-6D shows blood-brain barrier penetration of isofagomine tartrate and (3R,4R,5S)-5-(difluoromethyl)piperidine-3,4-diol fumarate in rats;

FIGS. 8A-8B show GCase activity in brain and liver of N370S and L444P mice after administration of isofagomine tartrate and (3R,4R,5S)-5-(difluoromethyl)piperidine-3,4-diol fumarate;

FIGS. 11A-11C show GCase activity in brain, liver and spleen of L444P mice after administration of (3R,4R,5S)-5-(difluoromethyl)piperidine-3,4-diol fumarate;

FIGS. 14A-14E show bone, marrow, brain, liver and spleen GlcSph levels of L444P mice after administration of (3R,4R,5S)-5-(difluoromethyl)piperidine-3,4-diol fumarate;

FIGS. 15A-15C show GCase activity in brain, liver and spleen of L444P mice after administration of (3R,4R,5S)-5-(difluoromethyl)piperidine-3,4-diol fumarate;

FIGS. 16A-16C show, brain, liver and spleen GlcCer levels of L444P mice after administration of (3R,4R,5S)-5-(difluoromethyl)piperidine-3,4-diol fumarate;

FIGS. 17A-17C show, brain, liver and spleen GlcSph levels of L444P mice after administration of (3R,4R,5S)-5-(difluoromethyl)piperidine-3,4-diol fumarate;

FIGS. 20A-20F show brain, liver and spleen GCase activity of L444P mice across 3 studies after administration of (3R,4R,5S)-5-(difluoromethyl)piperidine-3,4-diol fumarate; and FIGS. 21A-21F show brain, liver and spleen GlcSph levels of L444P mice across 3 studies after administration of (3R,4R,5S)-5-(difluoromethyl)piperidine-3,4-diol fumarate.

DETAILED DESCRIPTION

Figure 1:
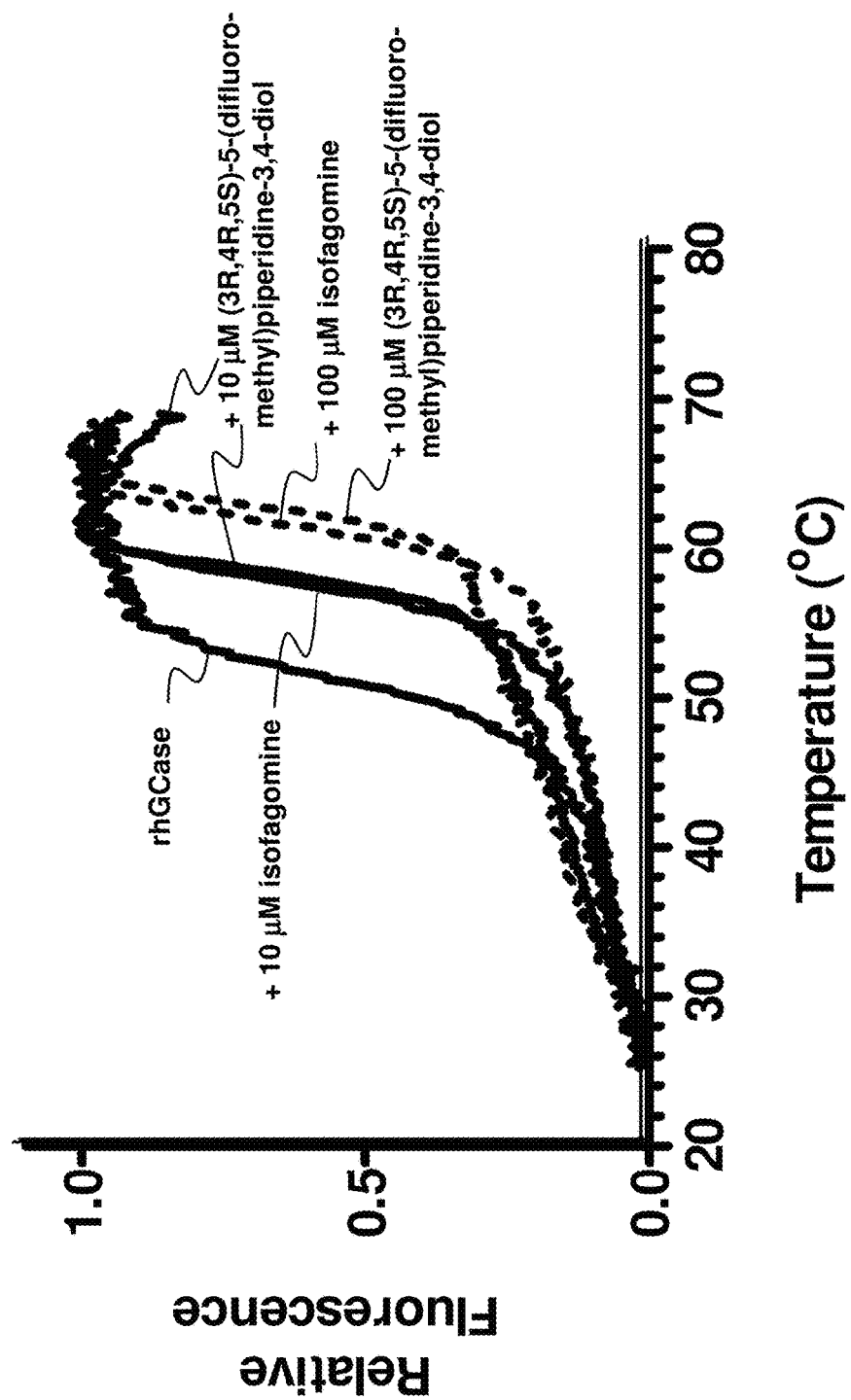
FIG. 1 shows an in vitro thermal stability assay of rhGCase in the presence and absence of a salt of isofagomine and a salt of (3R,4R,5S)-5-(difluoromethyl)piperidine-3,4-diol.

Many degenerative disorders of the central nervous system are associated with pathologic aggregation of proteins or lipids. For example, synucleinopathies are a group of diseases that arise from disruption of synuclein protein homeostasis. In particular, alpha-synuclein aggregation is associated with pathological conditions characterized by Lewy bodies, such as Parkinson's disease, Lewy Body Dementia (LBD), and multiple system atrophy. Likewise, alpha-synuclein fragment, non-Abeta component, is found in amyloid plaques of Alzheimer's disease.

Lewy bodies are present in a variety of dementia-based disorders and are not unique to Parkinson's disease. The accumulation of alpha-synuclein in Lewy bodies is very prevalent, and thus research efforts have been conducted to identify the possible function and role of alpha-synuclein in the pathology of Parkinson's disease and other Lewy body disorders. Transgenic mouse models harboring a mutant human A53T alpha-synuclein gene display symptoms similar to Parkinson's disease along with an abnormal accumulation of alpha-synuclein. One study found that when mutant alpha-synuclein expression is suppressed in older mice exhibiting symptoms of Parkinson's disease, a significant amount of alpha-synuclein pathology was cleared, hippocampal synaptic defects reverted, and the mice demonstrated improved memory function.

Alpha-synuclein represents a link between Gaucher disease and Parkinson's disease. Gaucher patients have reduced levels of GCase present in lysosomes, and GCase plays a role in the degradation of alpha-synuclein. Additionally, alpha-synuclein over-expression has been shown to inhibit vesicle transport between the Endoplasmic Reticulum (ER) and the Golgi apparatus, which is the main trafficking route by which GCase reaches the lysosome. While not wishing to be bound by any particular theory, there may be a positive feedback loop originating from the initial low GCase activity in the lysosome due to Gaucher disease, in which alpha-synuclein accumulates and continues to promote inhibition of vesicle transport between the ER and Golgi Apparatus. As patients age, the average concentration of alpha-synuclein continues to increase, leading to an increasingly higher inhibition of vesicle transport and thus more severe reduction of GCase transport to the lysosome. Alternately, the accumulation of the substrate glucocerebroside (GlcCer) due to low GCase activity may promote the formation of toxic alpha-synuclein oligomers in neurons.

The link between GCase N370S mutant and Parkinson's has been investigated, and the interaction in lysosomal conditions (pH 5.5) between GCase and alpha-synuclein was mapped. No complex between GCase and alpha-synuclein was observed at pH 7.4, suggesting that the complex is unable to form in pH ranges of the cytosol. A complex was mapped at pH 5.5, indicating that the lysosomal pH may be one of the primary environments in which this protein-protein interaction occurs. Further, the complex is destabilized by 25-200 mM NaCl, suggesting that the addition of NaCl disrupts electrostatic interactions that lead to complex formation. The N370S GCase mutant has a reduced affinity for alpha-synuclein. Immunoprecipitation and immunofluoresence verified the interaction in human tissue and neuronal cell culture, respectively. Alpha-synuclein and GCase interaction is favored in the lysosome, and the non-covalent interaction provides the groundwork to explore mechanisms that could be the basis for a link between GBA and Parkinson's disease. Alpha-synuclein is predominately degraded by lysosomes. Protein turnover is slowed in mice with lysosomal storage disorders, and thus a link between alpha-synuclein clearance and GCase levels could be linked. While not wishing to be bound by any particular theory, two hypotheses include: reduced GCase activity leads to accumulation of alpha-synuclein, or reduced ceramide metabolism triggers cell death. Lewy bodies may be a cellular response to altered ceramide concentration.

A number of studies have been conducted in an effort to identify the frequency of mutation in the GBA gene in patients with Parkinson's disease. Many studies, including ones conducted in Brazil, Venezuela, Portugal, Taiwan, Japan, and North Africa, show a higher incidence rate of GBA mutations in patients with Parkinson's disease as compared to the incidence rate of GBA mutations in a control group. A particularly notable association rate, 31% of patients as compared to 6% of the control population, was identified in the Ashkenazi Jewish population. One study in Norway did not find a higher rate of association of GBA mutations with Parkinson's patients as compared to the GBA mutation frequency in a control group. This study selected a control group that was appropriate for the age and sex composition of the experimental Parkinson's group, and considers the idea that the Ashkenazi study's control group demonstrated a higher frequency in GBA mutations associated with Parkinson's disease simply because GBA mutation homozygotes are much more common in that population. Overall, a higher rate of GBA association with Parkinson's disease suggests that GBA mutations could serve as a risk factor for Parkinson's disease. Further, one study suggests that the mutant allele presence operates in a dose-dependent manner. For example, patients harboring two N370S mutant alleles are at a higher risk for Parkinson's disease than those only carrying one mutant N370S allele. Some studies also suggest that patients with Parkinson's disease who are also harboring mutant GBA alleles demonstrate a disease onset at an earlier age than Parkinson's patients with wild-type GBA alleles.

As described above, enhancement of GCase activity in the brain has been shown to prevent accumulation of synuclein in the brain. Accordingly, agents and dosing regimens that enhance GCase activity are expected provide relief for patients at risk for developing or diagnosed with degenerative disorders of the central nervous system.

Definitions

As used herein the following terms shall have the definitions set forth below.

As used herein, the term "treating" means to ameliorate one or more symptoms associated with the referenced disorder.

As used herein, the term "preventing" means to impede or delay the onset of one or more symptoms associated with the referenced disorder.

As used herein the phrase "an effective amount" means an amount effective to prevent and/or treat a patient at risk for developing or diagnosed with the referenced disorder, and thus producing the desired therapeutic effect.

As used herein the term "patient" refers to a mammal (e.g., a human) at risk for developing or diagnosed with the referenced disorder.

As used herein the phrase "lysosomal storage disorder" refers to any of a group of diseases resulting from abnormal metabolism resulting in accumulation of a substrate in the lysosome.

As used herein, the phrase "degenerative disorder of the central nervous system" means any disorder associated with the premature degeneration of any component of the central nervous system, such as neurons, myelin sheaths or axons. Such disorders include but are not limited to alpha-synucleinopathies.

As used herein, the term "synucleinopathy" refers to diseases associated with aberrant accumulation of alpha-synuclein, including but not limited to parkinsonism, Parkinson's disease, Lewy Body Dementia, Multiple System Atrophy, Hallervorden-Spatz disease, and Frontotemporal Dementia.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Dosing Regimens for (3R,4R,5S)-5-(difluoromethyl)piperidine-3,4-diol

One aspect of the present invention provides dosing regimens for the treatment and/or prevention of lysosomal storage disorders such as Gaucher disease using (3R,4R,5S)-5-(difluoromethyl)piperidine-3,4-diol or a salt thereof. Another aspect of the present invention provides dosing regimens for the treatment and/or prevention of degenerative disorders of the central nervous system using (3R,4R,5S)-5-(difluoromethyl)piperidine-3,4-diol or a salt thereof. In one or more embodiments, the degenerative disorder of the central nervous system is a synucleinopathy, such Parkinson's disease or Lewy Body Dementia (LBD).

The compound (3R,4R,5S)-5-(difluoromethyl)piperidine-3,4-diol and some of its salts such as the hydrochloride salt are first described in U.S. Patent Publication Nos. 2011/

0091442 and 2011/0092541, the disclosures of which are incorporated by reference herein in their entireties. (3R,4R,5S)-5-(difluoromethyl)piperidine-3,4-diol is a small molecule that functions as a chaperone that binds to the active site of GCase, and this binding stabilizes the enzyme so that it is successfully transported from the Endoplasmic Reticulum to its destination, the lysosome. Although the small molecule (3R,4R,5S)-5-(difluoromethyl)piperidine-3,4-diol may initially function as a competitive inhibitor for GCase, a washout period ensures that the small molecule clears the lysosome after successful transport to the lysosome. During a washout period of the competitive inhibitor, the successfully transported enzymes are assured to react with the substrates glucosylceramide (GlcCer) and glucosylsphingosine (GlcSph) in the lysosome.

The free base form of (3R,4R,5S)-5-(difluoromethyl)piperidine-3,4-diol has the following structure, and is designated herein as Compound 1:

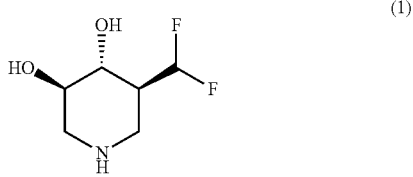 [SMILES: O[C@H]1[C@H](O)CNC[C@@H]1C(F)F]

(3R,4R,5S)-5-(difluoromethyl)piperidine-3,4-diol hydrochloride has the following structure, and is designated herein as Compound 2:

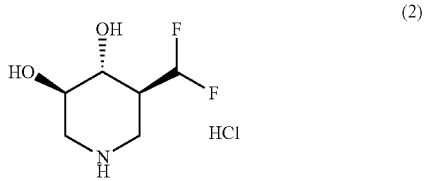 [SMILES: O[C@H]1[C@H](O)CNC[C@@H]1C(F)F ; Cl]

Additional salts of (3R,4R,5S)-5-(difluoromethyl)piperidine-3,4-diol are described in U.S. Patent Publication No. 2015/0050263, the disclosure of which is incorporated by reference herein in its entirety. One such salt is (3R,4R,5S)-5-(difluoromethyl)piperidine-3,4-diol fumarate having the following structure, and is designated herein as Compound 3:

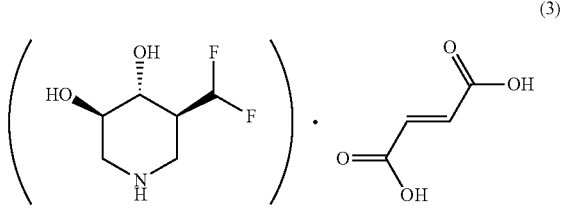

As used herein, the terms "(3R,4R,5S)-5-(difluoromethyl)piperidine-3,4-diol or salt thereof" or simply "(3R,4R,5S)-5-(difluoromethyl)piperidine-3,4-diol" refer to the free base form (Compound 1) or any pharmaceutically acceptable salt (e.g., Compound 2 or 3). Any situation meant to specifically refer to the free base form of (3R,4R,5S)-5-(difluoromethyl)piperidine-3,4-diol and not any salts thereof will specify "free base" or "Compound 1."

Pharmaceutically acceptable salts include, but are not limited to, acid addition salts, such as hydrochlorides, sulfates, nitrates, phosphates, perchlorates, borates, hydrohalides, acetates, tartrates, maleates, citrates, succinates, palmoates, methanesulfonates, benzoates, salicylates, benzenesulfonates, ascorbates, glycerophosphates, ketoglutarates, fumarates or tosylates. In some embodiments, the salt is a fumarate salt such as Compound 3.

As used herein, the term "free base equivalent" or "FBE" refers to the amount of (3R,4R,5S)-5-(difluoromethyl)piperidine-3,4-diol present in the (3R,4R,5S)-5-(difluoromethyl) piperidine-3,4-diol or salt thereof. In other words, the term "FBE" means either an amount of (3R,4R,5S)-5-(difluoromethyl)piperidine-3,4-diol free base, or the equivalent amount of (3R,4R,5S)-5-(difluoromethyl)piperidine-3,4-diol free base that is provided by a salt of (3R,4R,5S)-5-(difluoromethyl)piperidine-3,4-diol. For example, due to the weight of the fumarate anion, 16.94 grams of (3R,4R,5S)-5-(difluoromethyl)piperidine-3,4-diol fumarate (Compound 3) only provides as much (3R,4R,5S)-5-(difluoromethyl) piperidine-3,4-diol as 10 grams of the free base form (Compound 1). Other salts will have different conversion factors, depending on the molecular weight of the counter ion.

In one or more embodiments, the (3R,4R,5S)-5-(difluoromethyl)piperidine-3,4-diol or salt thereof is administered in a unique dosing regimen that balances the chaperoning and inhibitory effects of (3R,4R,5S)-5-(difluoromethyl)piperidine-3,4-diol. For example, the (3R,4R,5S)-5-(difluoromethyl)piperidine-3,4-diol may be administered for an enzyme enhancement period in which the (3R,4R,5S)-5-(difluoromethyl)piperidine-3,4-diol enhances GCase activity by facilitating proper folding, trafficking, non-aggregation, etc. After the enzyme enhancement period, the (3R,4R,5S)-5-(difluoromethyl)piperidine-3,4-diol may be not administered for a substrate turnover period to allow the (3R,4R,5S)-5-(difluoromethyl)piperidine-3,4-diol concentration to drop below inhibitory concentrations to enable the disassociation of the (3R,4R,5S)-5-(difluoromethyl)piperidine-3,4-diol from the GCase. The dosing regimen may include a second enzyme enhancement period, which may be the same as or different from the first enzyme enhancement period. The dosing regimen may include a second substrate turnover period, which may be the same or different from the first substrate turnover period. The dosing regimen may also include cycling between enzyme enhancement periods and substrate turnover periods.

The (3R,4R,5S)-5-(difluoromethyl)piperidine-3,4-diol or salt thereof may be administered once a day for up to 7 days a week. In various embodiments, the substrate turnover period is about 24 hours, about 48 hours, about 72 hour, or about 96 hours. The substrate turnover period is defined as the time between successive enzyme enhancement periods. For example, if the substrate turnover period is about 24 hours and the enzyme enhancement period consists of a single administration of the (3R,4R,5S)-5-(difluoromethyl) piperidine-3,4-diol or salt thereof, then the time between successive administrations is about 24 hours (i.e. once a day). Similarly, if the substrate turnover period is about 48 hours and the enzyme enhancement period consists of a single administration of the (3R,4R,5S)-5-(difluoromethyl) piperidine-3,4-diol or salt thereof, then the time between successive administrations is about 48 hours (i.e. every other day). Further examples include substrate turnover periods of about 72 hours (e.g. administration on Monday and Thursday but not Tuesday and Wednesday) or about 96 hours (e.g.

administration on Thursday and the following Monday but not on the Friday, Saturday or Sunday in between). The terms "about 24 hours", "about 48 hours", "about 72 hours" and "about 96 hours" do not require that the administrations be at the same time each administration day, but merely represent that the administrations occur on different days.

Examples of suitable dosing regimens include the following administrations:
 a. once a day for seven days a week (e.g. Monday-Sunday);
 b. once a day for three non-consecutive days a week (e.g. Monday, Wednesday, Friday); and
 c. once a day for two non-consecutive days a week (e.g. Monday and Thursday).

Each individual administration may include a therapeutically effective amount of (3R,4R,5S)-5-(difluoromethyl)piperidine-3,4-diol or a salt thereof. Each administration may include an amount of (3R,4R,5S)-5-(difluoromethyl)piperidine-3,4-diol or a salt thereof in the range from about 0.75 mg/kg FBE to about 3.5 mg/kg FBE or in the range from about 50 mg FBE to about 300 mg FBE. Exemplary amounts include 0.75 mg/kg FBE, 1 mg/kg FBE, 1.25 mg/kg FBE, 1.5 mg/kg FBE, 1.75 mg/kg FBE, 2 mg/kg FBE, 2.33 mg/kg FBE, 2.5 mg/kg FBE, 3 mg/kg FBE, or 3.5 mg/kg FBE. Exemplary amounts also include 50 mg FBE, 60 mg FBE, 70 mg FBE, 80 mg FBE, 90 mg FBE, 100 mg FBE, 110 mg FBE, 120 mg FBE, 130 mg FBE, 140 mg FBE, 150 mg FBE, 160 mg FBE, 175 mg FBE, 200 mg FBE, 250 mg FBE and 300 mg FBE. The amount administered during different administrations may be the same or the administered amount may vary.

Kits

Another aspect of present invention provides kits for the treatment and/or prevention of lysosomal storage disorders such as Gaucher disease, and/or kits for the treatment and/or prevention of degenerative disorders of the central nervous system such as the synucleinopathies Parkinson's disease or Lewy Body Dementia. The kit includes one or more dosage forms comprising an effective amount of the pharmacological chaperone. The kit may include instructions for administering the pharmacological chaperone according to any of the dosing regimens described herein. The kit may also include inactive dosage forms that do not include the pharmacological chaperone. Either the active and/or inactive dosage forms may include other therapeutic agents such as those suitable for combination therapy.

Formulations

The pharmacological chaperone can be formulated to be suitable for any route of administration, including e.g., orally in the form of tablets or capsules or liquid, or in sterile aqueous solution for injection. When the pharmacological chaperone is formulated for oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); or preservatives (e.g., methyl or propyl-p-hydroxybenzoates or sorbic acid). The liquid preparations may also contain buffer salts, flavoring, coloring or sweetening agents as appropriate. Preparations for oral administration may be suitably formulated to give controlled or sustained release of the compound.

In one or more embodiments of the present invention, the compound is administered in a dosage form that permits systemic distribution or uptake, such that the compound may cross the blood-brain barrier so as to exert effects on neuronal cells. Such dosage forms that permit systemic distribution or uptake may be oral or parenteral. In some embodiments, the compound may be distributed systemically, including crossing the blood-brain barrier. For example, pharmaceutical formulations of the compound suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, polyethylene glycol, and the like), suitable mixtures thereof, or vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate or gelatin.

Sterile injectable solutions are prepared by incorporating the compound in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a commonly used excipient.

The formulation can also contain a non-ionic detergent. Examples of non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

The therapeutic agent(s) may be administered orally or parenterally, including intravenously, subcutaneously, intra-arterially, intraperitoneally, ophthalmically, intramuscularly, buccally, rectally, vaginally, intraorbitally, intracerebrally, intradermally, intracranially, intraspinally, intraventricularly, intrathecally, intracisternally, intracapsularly, intrapulmonarily, intranasally, transmucosally, transdermally, or via inhalation. In one preferred embodiment, the therapeutic agent(s) is administered orally.

Administration of therapeutic agent(s) may be by periodic injections of a bolus of the formulation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

A suitable pharmaceutical preparation is in a unit dosage form. In such form, the preparation is subdivided into suitably sized unit doses containing appropriate quantities of the active component, e.g., an effective amount to achieve the desired purpose.

Combination Drug Therapy

The (3R,4R,5S)-5-(difluoromethyl)piperidine-3,4-diol or salt thereof can be administered in combination with at least one other therapeutic agent. Administration of the (3R,4R,5S)-5-(difluoromethyl)piperidine-3,4-diol or salt thereof in combination with at least one other therapeutic agent is understood to encompass administration that is sequential or concurrent. In one embodiment, the therapeutic agents are administered in separate dosage forms. In another embodiment, two or more therapeutic agents are administered concurrently in the same dosage form.

Examples of suitable therapeutic agents to administer in combination with the (3R,4R,5S)-5-(difluoromethyl)piperidine-3,4-diol or salt thereof can be found in U.S. Patent Publication Nos. 2011/0091442 and 2011/0092541, which are incorporated by reference in their entireties above.

For treating Parkinson's disease, the (3R,4R,5S)-5-(difluoromethyl)piperidine-3,4-diol or salt thereof can be administered in combination with at least one other therapeutic agent which includes but is not limited to, RNAi, dopamine replacement (e.g., levadopa (L-DOPA)), dopamine replacement stabilizer (e.g., carbidopa, and entacapone), anticholinergic (e.g., trihexyphenidyl, benzotropine mesylate (Cogentin®), trihexyphenidyl HCL (Artane®), and procyclidine), catechol-O-methyltransferase (COMT) inhibitor (e.g., entacapone (Comtan®) and tolcapone (Tasmar®)), dopamine receptor agonist (e.g., bromocriptine (Parlodel®), pramipexole (Mirapex®), ropinirole (Requip®)), pergolide (Permax), and APOKYN™ injection (apomorphine hydrochloride), monoamine oxidase (MAO) inhibitor (i.e., MAO-A and/or MAO-B inhibitors, e.g., selegiline (Deprenyl, Eldepryl®, Carbex®), selegiline HCI orally disintegrating tablet (Zelapar®), and rasagiline (Azilect®)), peripheral decarboxylase inhibitor, amantadine (Symmetrel®), and rivastigmine tartrate (Exelon®). In a particular embodiment for treating Parkinson's disease, the (3R,4R,5S)-5-(difluoromethyl)piperidine-3,4-diol or salt thereof is co-administered with a second therapeutic agent selected from the group consisting of carbidopa, levodopa, dopamine receptor agonists, anticholinergics, monoamide MAO inhibitors, and COMT inhibitors.

In a particular embodiment for treating Gaucher disease, the (3R,4R,5S)-5-(difluoromethyl)piperidine-3,4-diol or salt thereof is administered in combination with a second therapeutic agent selected from the group consisting of human recombinant β-glucocerebrosidase and miglustat. Examples of human recombinant β-glucocerebrosidase for enzyme replacement therapy include imiglucerase (Cerezyme®, available from Genzyme Corporation in Cambridge, Mass., USA). In a specific embodiment, the second therapeutic agent is human recombinant β-glucocerebrosidase. In an alternate embodiment, the second therapeutic agent is miglustat.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

In Vitro Thermal Stability Assay

An in vitro thermal stability assay of recombinant human GCase (rhGCase) was conducted to assess changes in enzyme stability in vitro at neutral pH in the presence of a salt of isofagomine or a salt of (3R,4R,5S)-5-(difluoromethyl)piperidine-3,4-diol. A dye (SYPRO® Orange) that fluoresces when it binds to hydrophobic regions of enzyme was used to assess stability, because unstable enzyme that loses its native conformation likely exposes internal hydrophobic amino acids, leading to an increase in fluorescence. The results of this assay are shown in FIG. 1.

In FIG. 1, the assay was normalized to a maximum fluorescence of 1.0, and the increase in fluorescence indicates unfolding of protein. The wild-type enzyme alone reached peak fluorescence at approximately 53° C., while 100 μM isofagomine increased the peak fluorescence to 63°

C., and 100 µM (3R,4R,5S)-5-(difluoromethyl)piperidine-3,4-diol increased peak fluorescence to 65° C. This shift indicates that the small molecule chaperone stabilizes the protein in vitro, because a higher temperature is required to elicit a maximum fluorescence response, suggesting that the protein remains folded at higher temperatures (for example, unfolding occurs at 65° C. with 100 µM (3R,4R,5S)-5-(difluoromethyl)piperidine-3,4-diol, instead of 53° C. alone) because the fluorescence corresponds with unfolded protein.

Example 2

Ex Vivo Enzyme Activity Assay

Figure 2:
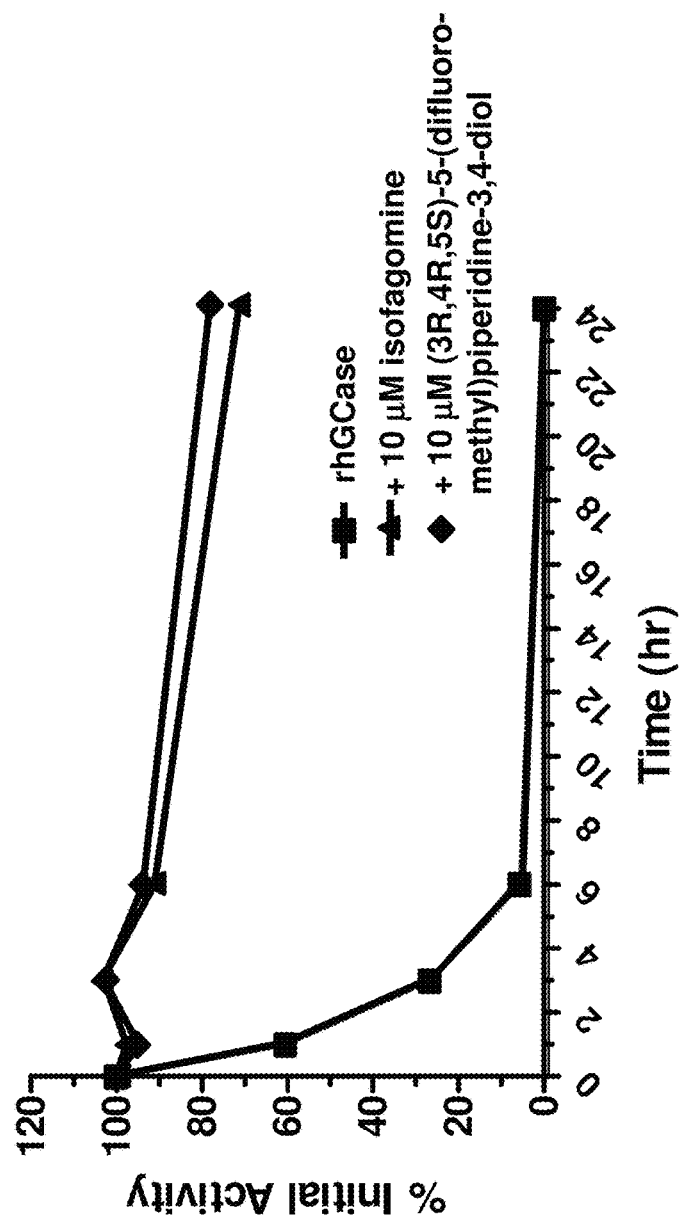
FIG. 2 shows an in vitro assay of rhGCase enzyme activity in ex vivo human blood in the presence and absence of a salt of isofagomine and a salt of (3R,4R,5S)-5-(difluoromethyl)piperidine-3,4-diol.

In vitro enzyme activity assays were conducted in human whole blood at 37° C. ex vivo to assess rhGCase enzyme activity in the presence of a salt of isofagomine or a salt of (3R,4R,5S)-5-(difluoromethyl)piperidine-3,4-diol. As shown in FIG. 2, enzyme activity in whole blood dropped below 10% initial activity after 6 hours, and decayed to almost 0% after 24 hours. With the administration of 10 µM isofagomine or 10 µM (3R,4R,5S)-5-(difluoromethyl)piperidine-3,4-diol, measured GCase activity remained higher for much longer, and remained above 60% for longer than 24 hours. This ex vivo assay shows that the small molecule chaperone is effective in increasing the length and efficacy of recombinant enzyme activity after administration.

Example 3

Enzyme Activity in Rats

After demonstrating stabilization of the enzyme ex vivo, a rat study was conducted using oral administration of a salt of isofagomine and a salt of (3R,4R,5S)-5-(difluoromethyl) piperidine-3,4-diol to determine if the compounds alter the circulating half-life of active rhGCase. Recombinant GCase was administered via IV bolus 30 minutes after oral gavage of 3 mg/kg of either isofagomine or (3R,4R,5S)-5-(difluoromethyl)piperidine-3,4-diol, and blood plasma GCase activity levels were measured at regular intervals. Both isofagomine (FIG. 3A) and (3R,4R,5S)-5-(difluoromethyl) piperidine-3,4-diol (FIG. 3B) sustained a higher normalized GCase activity in plasma longer than the administration of recombinant GCase alone. Additionally, western blot data shows more intense rhGCase bands when chaperone is included, as compared to GCase administration without an oral chaperone dose. Specifically, at the "5 minute" and "10 minute" interval of both isofagomine (FIG. 3C) and (3R, 4R,5S)-5-(difluoromethyl)piperidine-3,4-diol (FIG. 3D), a more intense protein band can be seen under the "3" (3 mg/kg chaperone) column than the "0" (no chaperone) column.

Example 4

Washout, Inhibition and Enhancement

To evaluate the potential therapeutic effect of a chaperone, the washout period can be examined to determine the length of time required to washout the inhibitor. Otherwise, enzyme that is successfully trafficked to the lysosome may not have optimal functionality because the chaperone, which also functions as a competitive inhibitor, can continue to compete with the substrate for the enzyme active site. As shown in FIG. 4A, (3R,4R,5S)-5-(difluoromethyl)piperidine-3,4-diol exhibits a lysosomal half-life of approximately 2.1 hours and a half-life in brain tissue of approximately 1.4 hours. In contrast, isofagomine exhibits a higher lysosomal half-life of approximately 8 hours, and a higher brain half-life of approximately 3 hours.

Figure 4B:
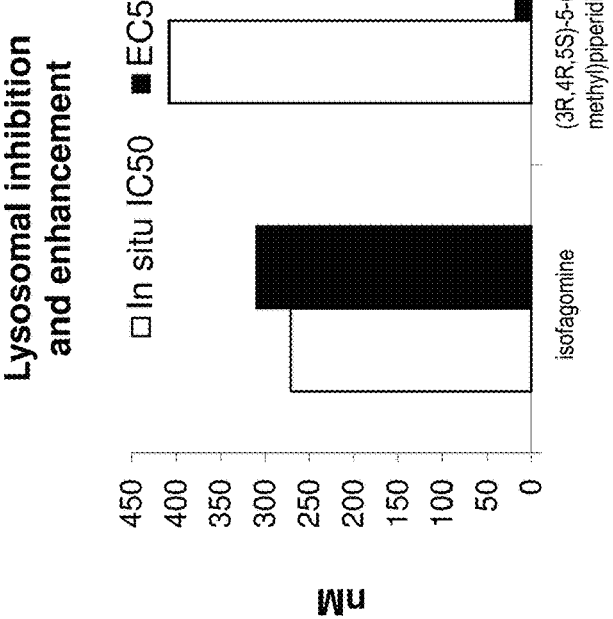
FIG. 4B shows lysosomal inhibition and enhancement with isofagomine and (3R,4R,5S)-5-(difluoromethyl)piperidine-3,4-diol.
Figure 4A:
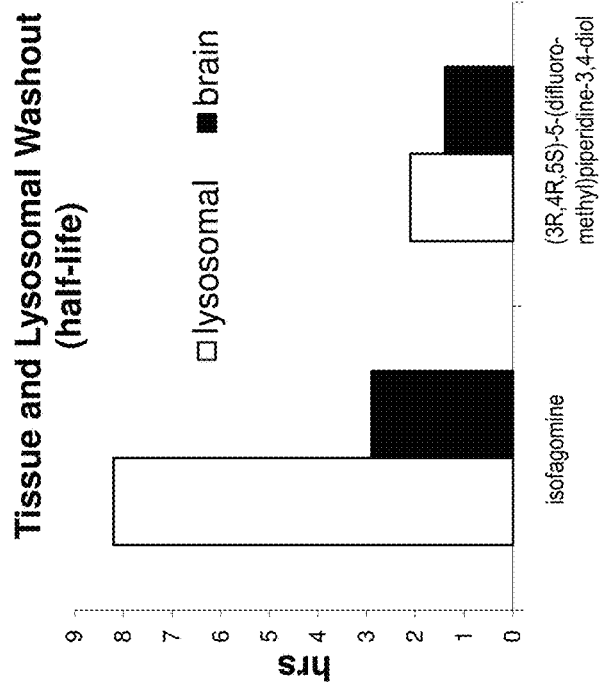
FIG. 4A shows tissue and lysosomal washout of isofagomine and (3R,4R,5S)-5-(difluoromethyl)piperidine-3,4-diol.

In FIG. 4B, IC50 and EC50 were determined in order to evaluate the potential for therapeutic effect, along with the potency of the binding of chaperone to enzyme. Isofagomine showed an IC50 value of 271 nM, while (3R,4R,5S)-5-(difluoromethyl)piperidine-3,4-diol showed an IC50 value of 408 nM. These data suggest that (3R,4R,5S)-5-(difluoromethyl)piperidine-3,4-diol is a less potent inhibitor of the enzyme than isofagomine because a higher molarity of (3R,4R,5S)-5-(difluoromethyl)piperidine-3,4-diol is required to reach 50% inhibition (408 nM). Additionally, (3R,4R,5S)-5-(difluoromethyl)piperidine-3,4-diol is effective at enhancing enzyme activity at a notably lower concentration, reaching a 50% of maximum (EC50) response at a concentration of 18 nM, while isofagomine does not reach 50% enhancement until it is present at a concentration of 310 nM. Notably, the drastic difference between IC50 and EC50 for (3R,4R,5S)-5-(difluoromethyl)piperidine-3,4-diol (408 nM and 18 nM, respectively) indicates that the drug reaches 50% effectiveness at 18 nM, which is far below its 50% inhibitory concentration of 408 nM.

Figure 5:
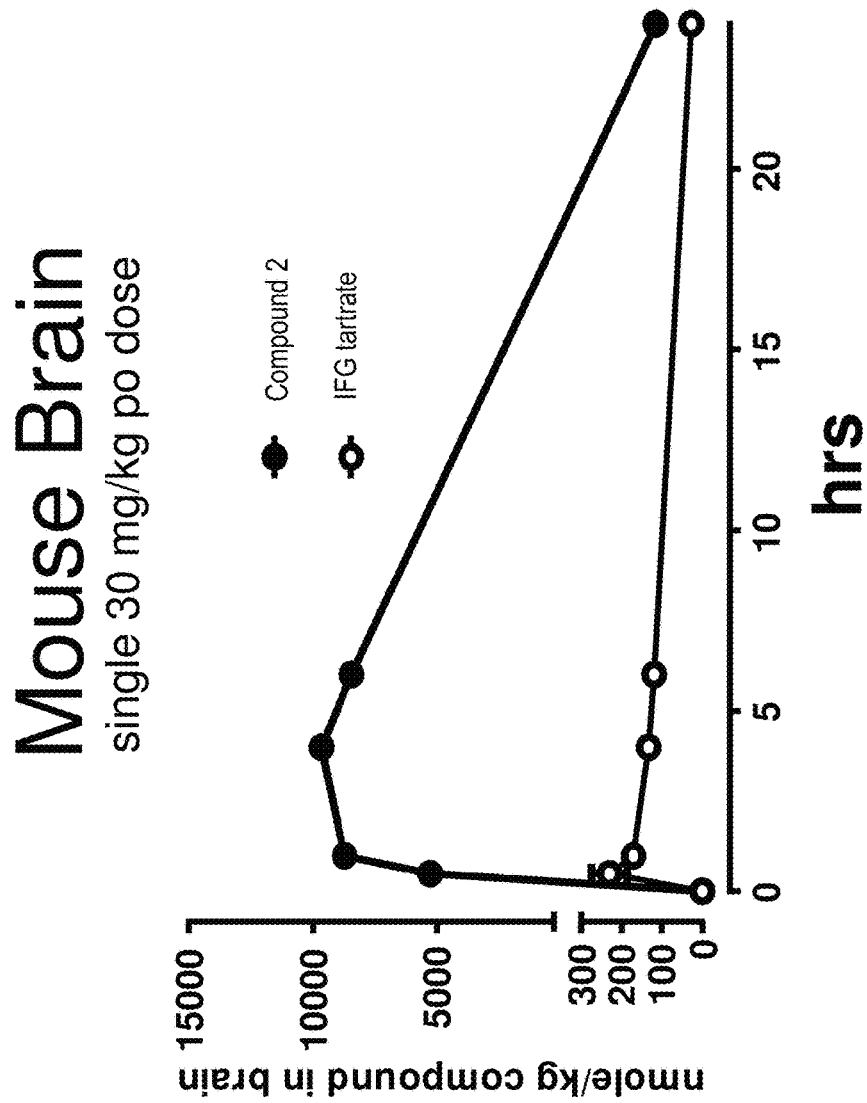
FIG. 5 shows blood-brain barrier penetration of isofagomine tartrate and (3R,4R,5S)-5-(difluoromethyl)piperidine-3,4-diol hydrochloride in mice.

The ability of a drug to penetrate the blood-brain barrier can be an important function. Without the capability of penetrating into the brain, the drug will not likely have a therapeutic effect in tissues in the brain. In FIG. 5, Compound 2 and isofagomine tartrate (IFG tartrate) were measured in mice that were sacrificed after exposure to these compounds, to assess drug distribution in the brain tissue. Both Compound 2 and IFG tartrate are capable of crossing the blood-brain barrier and thus have the capacity to exhibit their effects in the brain as well as other tissues. This penetration is beneficial for the treatment of Type II or III Gaucher disease in which patients exhibit central nervous system (CNS) pathology. With an oral dose of 30 mg/kg FBE of Compound 2, mouse brain tissues showed a peak compound concentration of 9.7 µM. With the same dose of IFG tartrate, the concentration of IFG tartrate in the brain only reached 30 nM.

A summary of the inhibition constants, blood-brain barrier penetration information and other parameters for IFG and (3R,4R,5S)-5-(difluoromethyl) piperidine-3,4-diol is in Table 1 below:

TABLE 1

| | Isofagomine | (3R,4R,5S)-5-(difluoromethyl) piperidine-3,4-diol |
|---|---|---|
| Ki pH 5.2 (nM) | 26 | 14 |
| Ki pH 7 (nM) | 4 | 3 |
| EC50 (N370S) (nM) | 310 | 18 |
| IC50 (in situ, nM) | 271 | 408 |
| Washout (in situ, hrs) | 8.2 | 2.1 |
| Emax | 94% | 106% |
| Bioavailability (plasma as percent oral dose) | 53% | 106% |
| Brain Cmax at 30 mg/kg (µM) | 0.3 | 9.7 |
| Plasma Cmax at 30 mg/kg (µM) | 17.5 | 84.5 |
| Barin/Plasma Cmax (%) | 1.65% | 11.48% |
| Brain tissue efflux (half-life, hrs) | 2.9 | 1.4 |
| ED50 in brain (mg/kg) | 56.4 | 5.2 |
| pKa | 8.4 | 7.1 |

Example 5

Blood-Brain Barrier Penetration in Rats

In FIGS. 6A-D, blood-brain barrier penetration was measured for Compound 3 and IFG tartrate in rats after a single 100 mg/kg FBE p.o. dose of each compound. FIGS. 6A and B show that the total brain exposure (in nM-hr) was 29% of plasma exposure (in nM-hr) for IFG tartrate, whereas FIGS. 6C and D show that the total brain exposure was 85% of plasma for Compound 3. Compound 3 had a 14-fold higher plasma exposure than IFG tartrate, and Compound 3 had a 39-fold higher brain exposure than IFG tartrate. Accordingly, not only was Compound 3 more bioavailable than IFG tartrate, but Compound 3 was also much more effective in crossing the blood-brain barrier.

Example 6

Dosing of IFG Tartrate and Compound 3 in N370S and L444P Mice

The purpose of this study was to first confirm that the GlcSph substrate was elevated in N370S and L444P mutant mouse models. Second, the GCase enzyme activity was to be evaluated after N370S mice were dosed with IFG tartrate, and after L444P mice were dosed with Compound 3. These dosing schemes were followed by a tissue examination to determine if exposure to the compounds reduced GlcSph or GlcCer substrate levels in the following tissues: brain, liver, spleen, and blood plasma.

As can be seen from Table 2 below, both the N370S and L444P mice showed a phenotype in which a higher level of GlcSph accumulated in the brain, liver, and spleen, as compared to the wild-type control mouse.

TABLE 2

|         |                      | ng/g (ml) GlcSph |       |        |         | µg/g GlcCer |       |        |        |
|---------|----------------------|------|-------|--------|---------|-------|-------|--------|--------|
|         |                      | Brain | Liver | Spleen | Plasma | Brain | Liver | Spleen | Plasma |
| Control | 9-11 wks (pilot)     | 19   | 7.0   | 18     | <0.5*   | 11    | 61    | 195    | 5*     |
| N370S   | 9-11 wks (pilot)     | 172  | 416   | 1,017  | 7*      | 13    | 74    | 315    | 6.8*   |
|         | 14 wks (Example 6)   | 239  | 435   | 1,118  | 7.9     | 6.2   | 83    | 355    | nm     |
| L444P   | 9-11 wks (pilot)     | 138  | 369   | 939    | 8*      | 11    | 65    | 236    | 5.7*   |
|         | 14 wks (Example 6)   | 202  | 430   | 1,356  | 8.4     | 9.1   | 86    | 305    | nm     |

Figure 7:
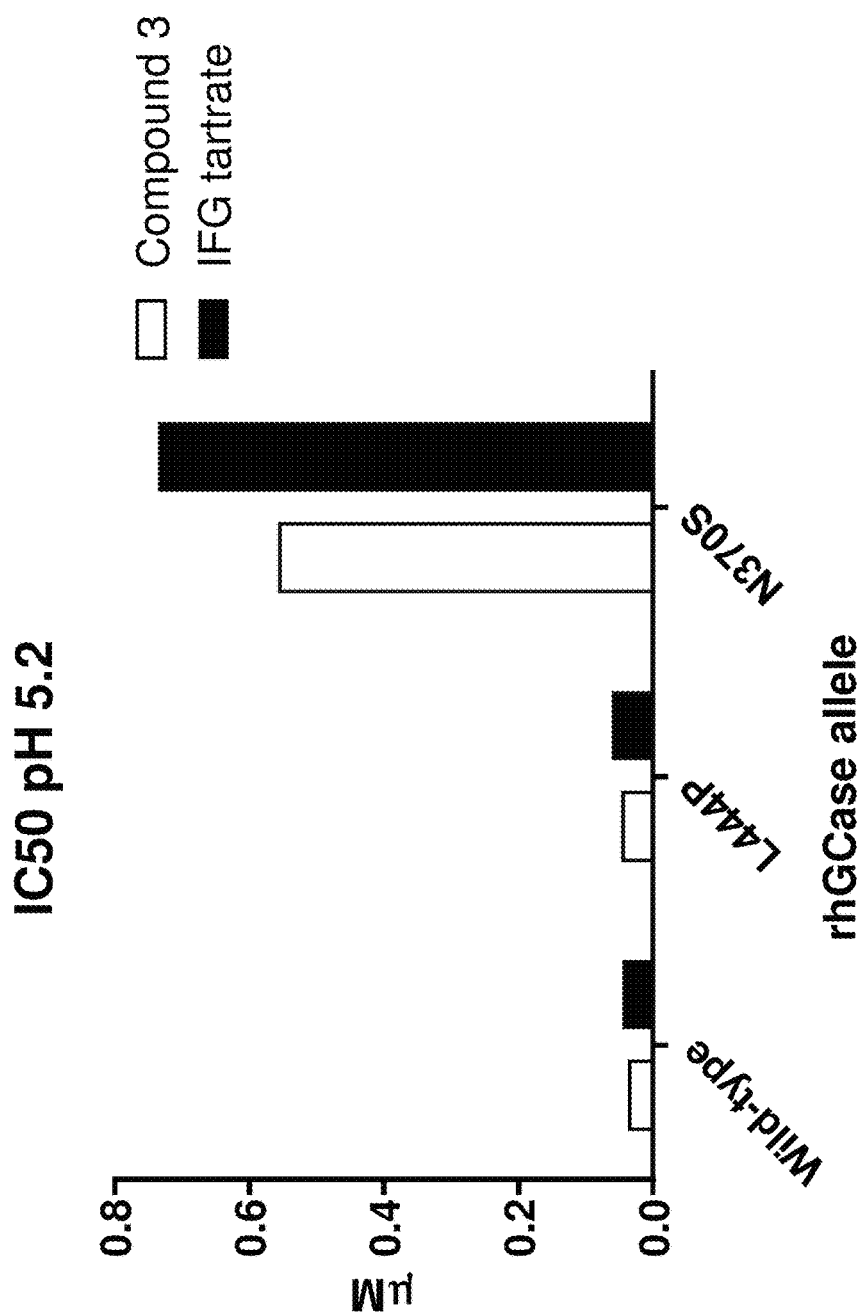
FIG. 7 shows IC50 values of isofagomine tartrate and (3R,4R,5S)-5-(difluoromethyl)piperidine-3,4-diol fumarate in rhGCase enzyme mutants.

Purified recombinant GCase enzyme mutants were used to determine IFG tartrate and Compound 3 IC50 values. The IC50 value is an indication of a concentration of drug required to inhibit 50% of the enzyme, and higher IC50 values indicate that a higher concentration of drug is required to achieve 50% inhibition. As shown in FIG. 7, both IFG tartrate and Compound 3 had IC50 values in the 50 nM range for wild-type and L444P enzyme mutants, suggesting a stronger interaction between these enzymes and small molecules than with the N370S mutant. For the N370S mutant, Compound 3 showed an IC50 value of 556 nM and IFG tartrate showed an IC50 value of 735 nM, suggesting a weaker interaction between these small molecules and the N370S mutant than with the L444P mutant or wild-type enzyme, because a much higher concentration of the small molecule was required to achieve 50% inhibition of the N370S mutant enzyme. A summary of the IC50 data is provided in Table 3 below:

TABLE 3

| rhGCase   | (3R,4R,5S)-5-(difluoromethyl) piperidine-3,4-diol (IC50, µM) | Isofagomine (IC50, µM) |
|-----------|-----------|-----------|
| Wild-type | 0.036     | 0.046     |
| L444P     | 0.046     | 0.061     |
| N370S     | 0.556     | 0.735     |

In FIG. 8, IFG tartrate was administered to N370S mutant mice daily at 100 mg/kg FBE, while Compound 3 was administered to L444P mice daily at 10 mg/kg FBE. Administration of Compound 3 to L444P mice enhanced GCase activity in the brain by 2.8 fold, and was almost equivalent to wild-type activity (FIG. 8A). Additionally, Compound 3 enhanced GCase activity by 7.6 fold in L444P liver (FIG. 8B).

Figure 9A:
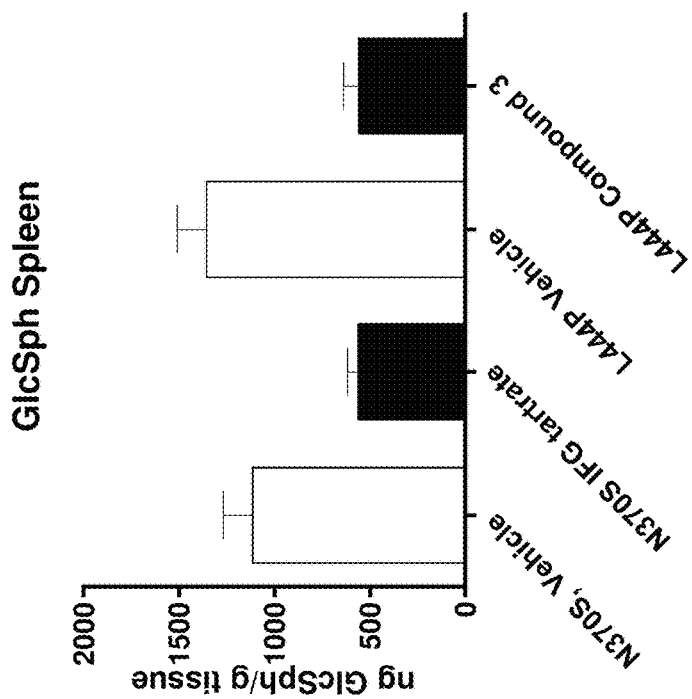
FIGS. 9A-9B show GlcSph levels in liver and spleen of N370S and L444P mice after administration of isofagomine tartrate and (3R,4R,5S)-5-(difluoromethyl)piperidine-3,4-diol fumarate.
Figure 9B:
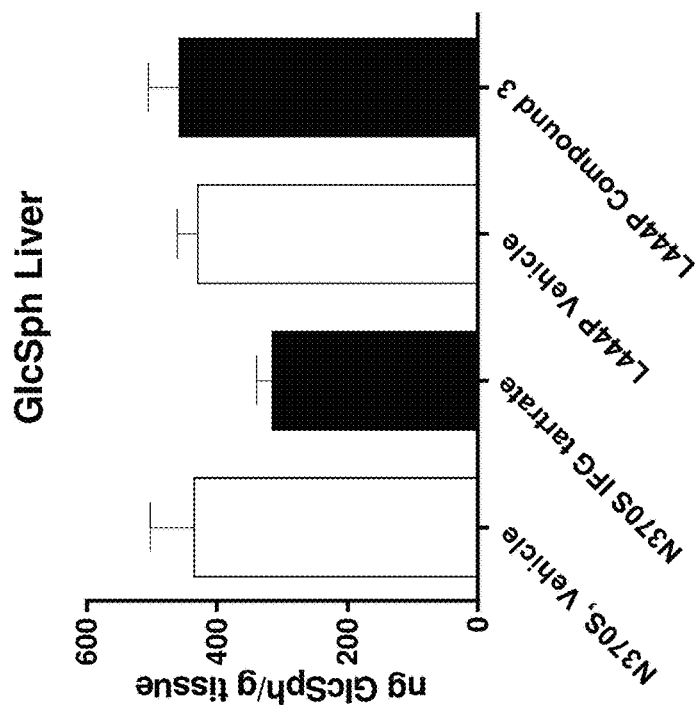

In FIG. 9, IFG tartrate was administered to the N370S mutant mice at 100 mg/kg FBE, and Compound 3 was administered to the L444P mutants at 10 mg/kg FBE. Both compounds were administered daily via an oral route. IFG tartrate showed a reduction in GlcSph substrate in the liver (FIG. 9A), and both IFG tartrate and Compound 3 showed a significant reduction of GlcSph in the spleen, compared to the control (FIG. 9B).

Figures 10A, 10B:
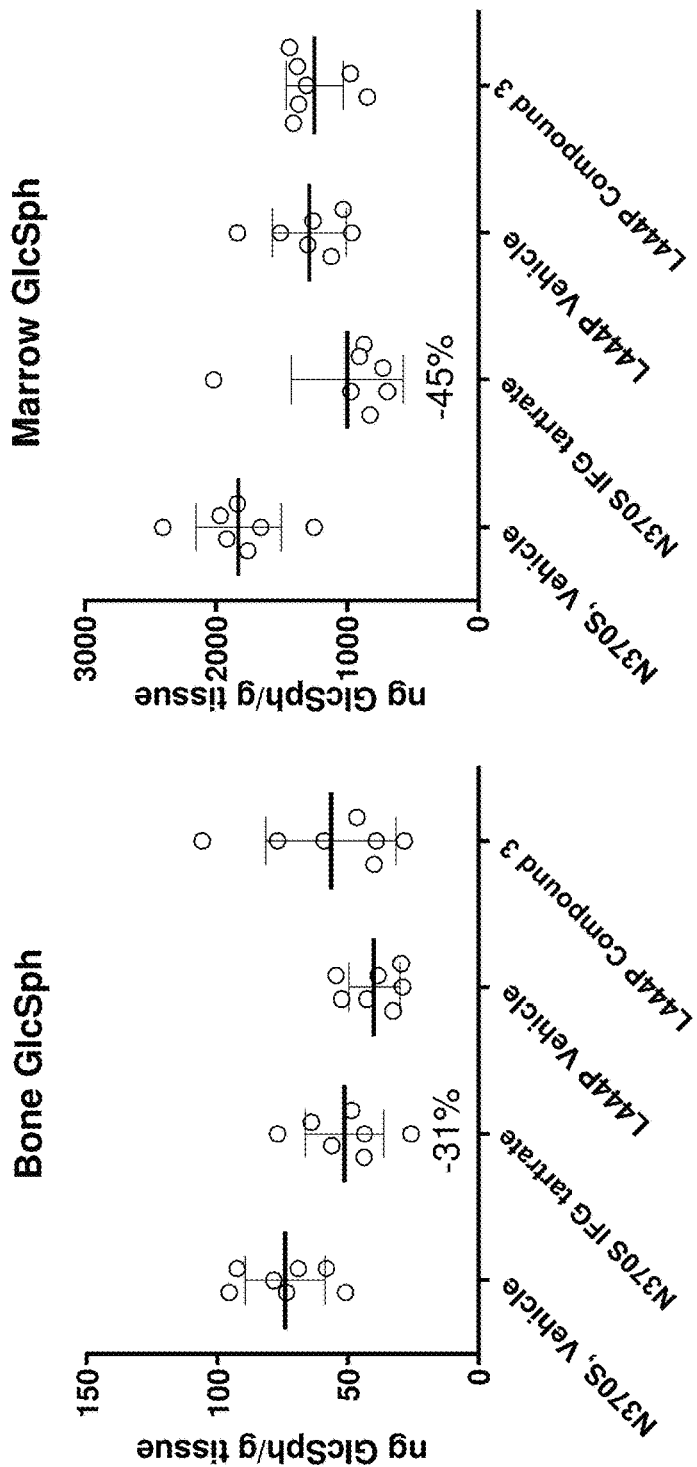
FIGS. 10A-10B show GlcSph levels in bone and marrow of N370S and L444P mice after administration of isofagomine tartrate and (3R,4R,5S)-5-(difluoromethyl)piperidine-3,4-diol fumarate.

In FIG. 10, both the N370S and L444P mouse models showed an elevated level of GlcSph in the bone (FIG. 10A) and marrow (FIG. 10B). After administration with IFG tartrate, N370S mice showed a reduction of 31% in bone GlcSph concentration, and a reduction of 45% GlcSph in marrow.

Example 7

Daily Dosing of Compound 3 in L444P Mice

The purpose of this study was to confirm reduction of the substrates GlcCer and GlcSph with different oral daily dosing regimens of Compound 3 given to L444P mice over a four week period. Both fixed and ascending dosing schemes were used and were administered in drinking water. Four fixed dose groups, 0.01 mg/kg FBE, 0.1 mg/kg FBE, 1 mg/kg FBE, and 10 mg/kg FBE were used. A fifth group, which used an ascending dose, was also included, and it began at 0.01 mg/kg FBE and increased by 10-fold each week, with a dose during the final week of 10 mg/kg FBE.

In FIG. 11, the 1 mg/kg FBE dose and the ascending 0.01-10 mg/kg FBE dose of Compound 3 showed a significant difference in measured GCase activity as compared to the vehicle in brain (FIG. 11A), liver (FIG. 11B), and spleen (FIG. 11C). A 1 mg/kg FBE dose showed almost a two-fold increase in brain GCase activity, a 5-fold increase in liver GCase activity, and a two-fold increase in spleen GCase activity. The ascending dose showed an increased brain GCase activity of about three-fold, increased liver activity of about 8-fold, and increased spleen GCase activity of about 4 fold. Doses of 0.01 mg/kg FBE and 0.1 mg/kg FBE of Compound 3 did not show significant differences.

Figure 12A:
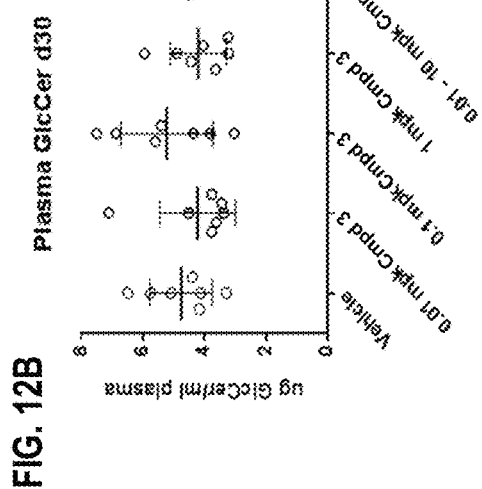
FIGS. 12A-12D show plasma GlcCer and GlcSph levels of L444P mice on days 1 and 30 of administration of (3R,4R,5S)-5-(difluoromethyl)piperidine-3,4-diol fumarate.
Figure 12B:
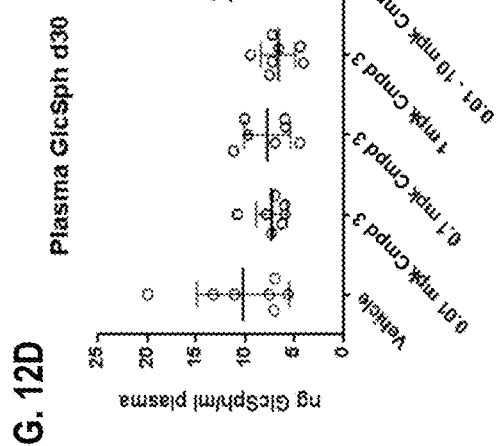
Figure 12C:
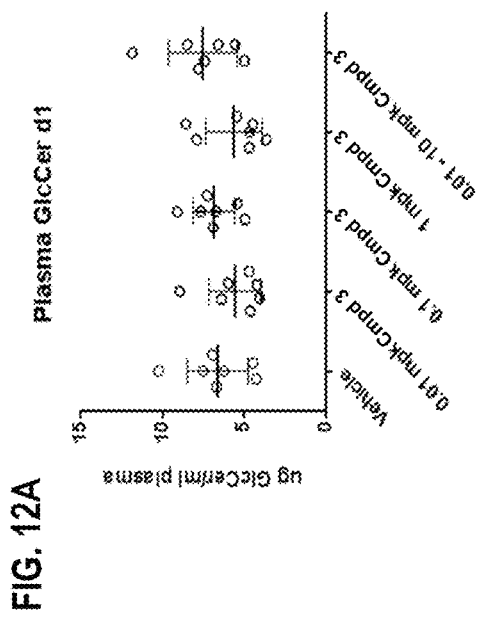
Figure 12D:
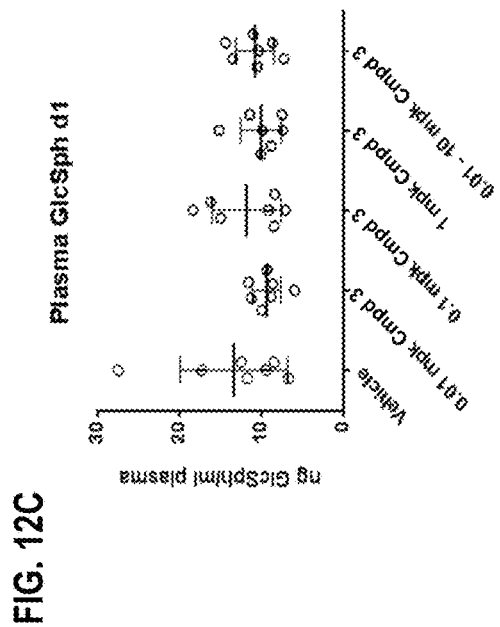

In FIG. 12, the concentration of substrates GlcCer and GlcSph were measured in plasma on Day 1 of daily oral dosing (FIGS. 12A and C, respectively), and again on Day 30, after a 24-hour washout period (FIGS. 12B and D, respectively). No groups were significantly different than the vehicle, indicating that there were no significant increases or decreases in plasma GlcCer and plasma GlcSph during the 30 day period.

Figure 13B:
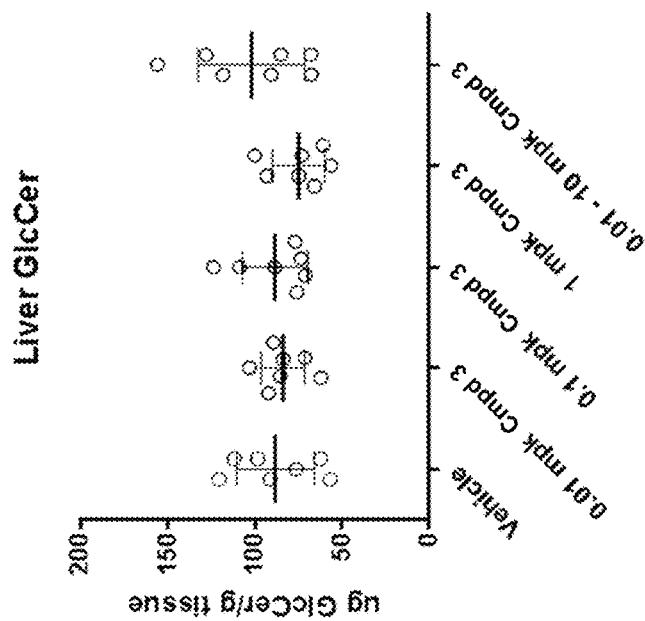
FIGS. 13A-13B show brain and liver GlcCer levels of L444P mice after administration of (3R,4R,5S)-5-(difluoromethyl)piperidine-3,4-diol fumarate.
Figure 13A:
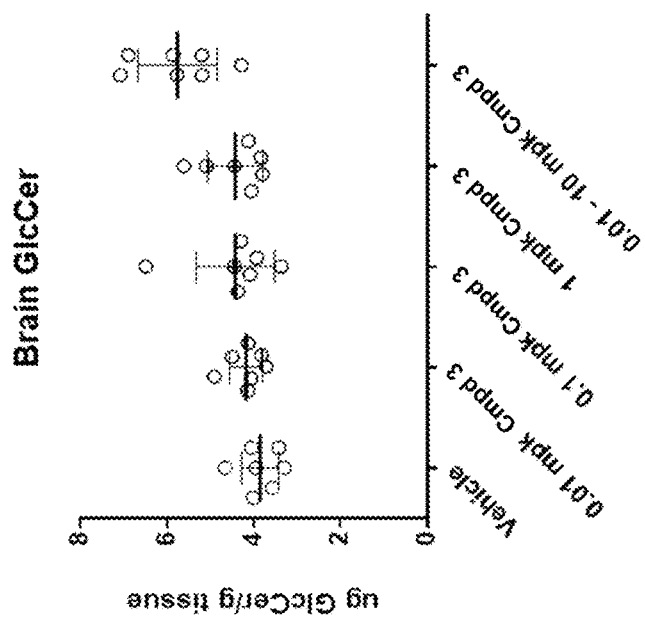

In FIG. 13, GlcCer concentrations were also measured in the brain (FIG. 13A) and liver (FIG. 13B) after 30 days, and there was a significant difference in substrate concentration in the brain between the vehicle and ascending dose regimens. No significant difference in GlcCer concentration was seen in the brain using 1 mg/kg FBE dosing. GlcCer concentration increased using the ascending dose scheme in the brain, as compared to vehicle. No significant differences in GlcCer concentration was seen in the liver.

Figure 14B:
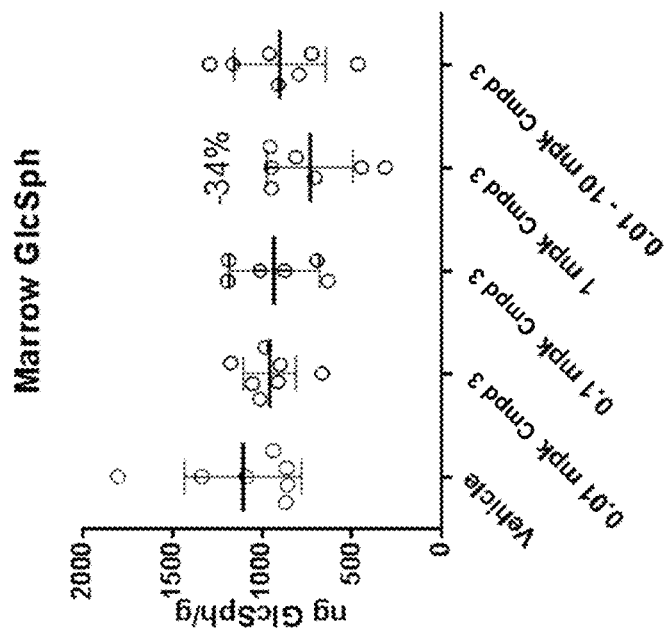
Figure 14A:
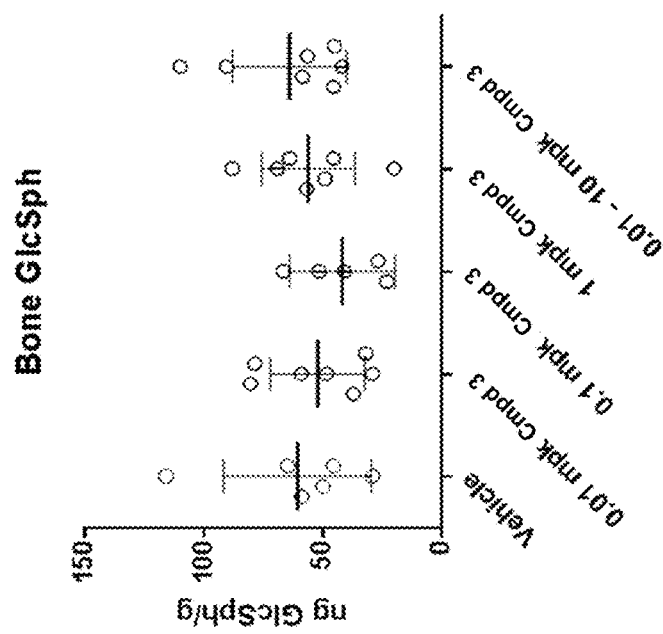

In FIG. 14, concentrations of the substrate GlcSph were also measured in bone (FIG. 14A), marrow (FIG. 14B), brain (FIG. 14C), liver (FIG. 14D) and spleen (FIG. 14E) using the same set of dosing regimens. Significant differences in the GlcSph substrate were seen in the brain, liver, and spleen. The ascending 0.01-10 mg/kg FBE dose showed an increase in substrate concentration in the brain as compared vehicle, but a reduction in concentration in the spleen. The 1 mg/kg FBE dose is also significantly different than the vehicle in the liver and spleen, showing an increase in GlcSph in the brain and a decrease in GlcSph in liver and spleen, as compared to vehicle.

Example 8

Additional Dosing Regimens of Compound 3 in L444P Mice

The purpose of this study was to improve dosing choices based on data collected from Example 7. Specific tissues of L444P mice that were measured were the liver, brain, spleen, bone, marrow, and plasma. The only dose in Example 7 that resulted in a significant elevation of brain GCase activity without a significant accumulation of brain GlcSph substrate was 1 mg/kg FBE, and this dose was used for further study. In Example 8, two dosing strategies were used, fixed dose and constant weekly dose. All doses were administered orally in drinking water. Fixed dose mice were given 1 mg/kg FBE either daily, two days a week, or three days a week. Constant weekly dose mice were given a total of 7 mg/kg FBE per week, either three days a week (Monday, Wednesday, Friday), two days a week (Monday, Thursday), or daily. For example, mice receiving 3 doses per week (Monday, Wednesday, Friday) would receive 2.33 mg/kg FBE in each dose, while mice receiving doses twice a week (Monday, Thursday) would receive 3.5 mg/kg FBE per dose.

Figures 15A, 15B, 15C:
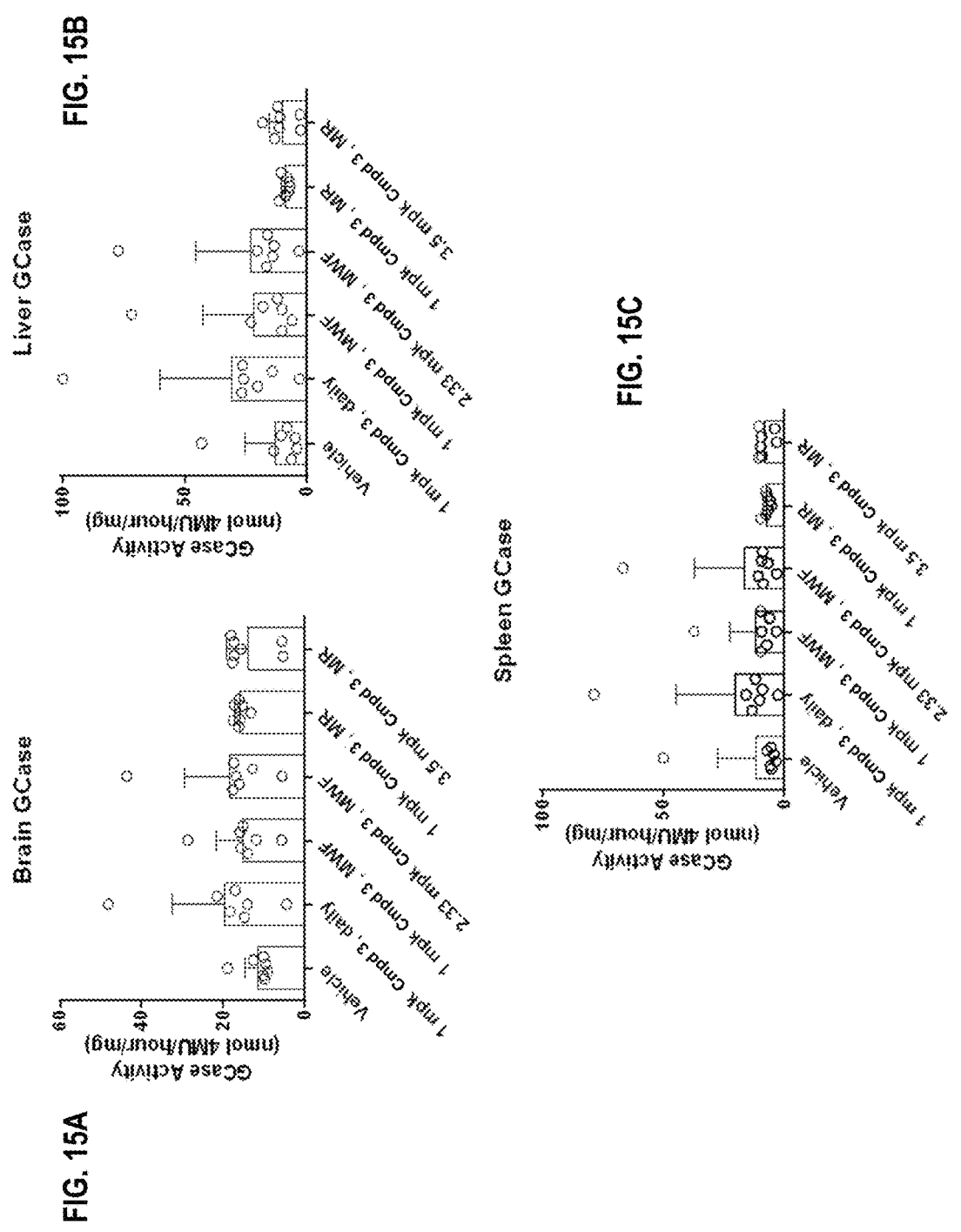

In FIG. 15, GCase activity was measured in the brain (FIG. 15A), liver (FIG. 15B), and spleen (FIG. 15C). As shown in FIG. 15A, GCase activity increased and was significant in the brain for the 1 mg/kg FBE daily dose.

In FIG. 16, brain (FIG. 16A), liver (FIG. 16B), and spleen (FIG. 16C) GlcCer substrate concentration was measured based on the different dosing regimens, and compared to vehicle. In FIG. 17, GlcSph substrate concentration was also measured in the brain (FIG. 17A), liver (FIG. 17B), and spleen (FIG. 17C). A significant reduction in GlcSph concentration in the liver and spleen was seen in the 1 mg/kg FBE daily dose of Compound 3 group, as compared to the vehicle.

Figure 18A:
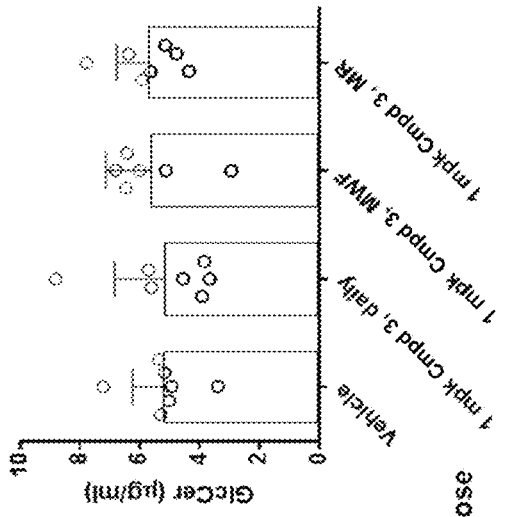
FIGS. 18A-18C show plasma GlcCer levels in L444P mice after various administration schedules of (3R,4R,5S)-5-(difluoromethyl)piperidine-3,4-diol fumarate.
Figure 18B:
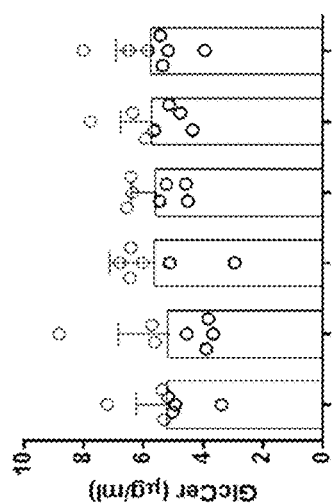
Figure 18C:
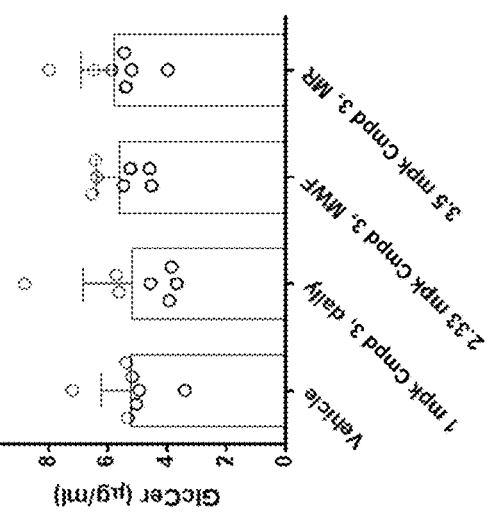

Plasma concentration of GlcCer was also measured as shown in FIGS. 18A-C, and across all doses no significant differences were seen in plasma concentrations of GlcCer.

Figure 19:
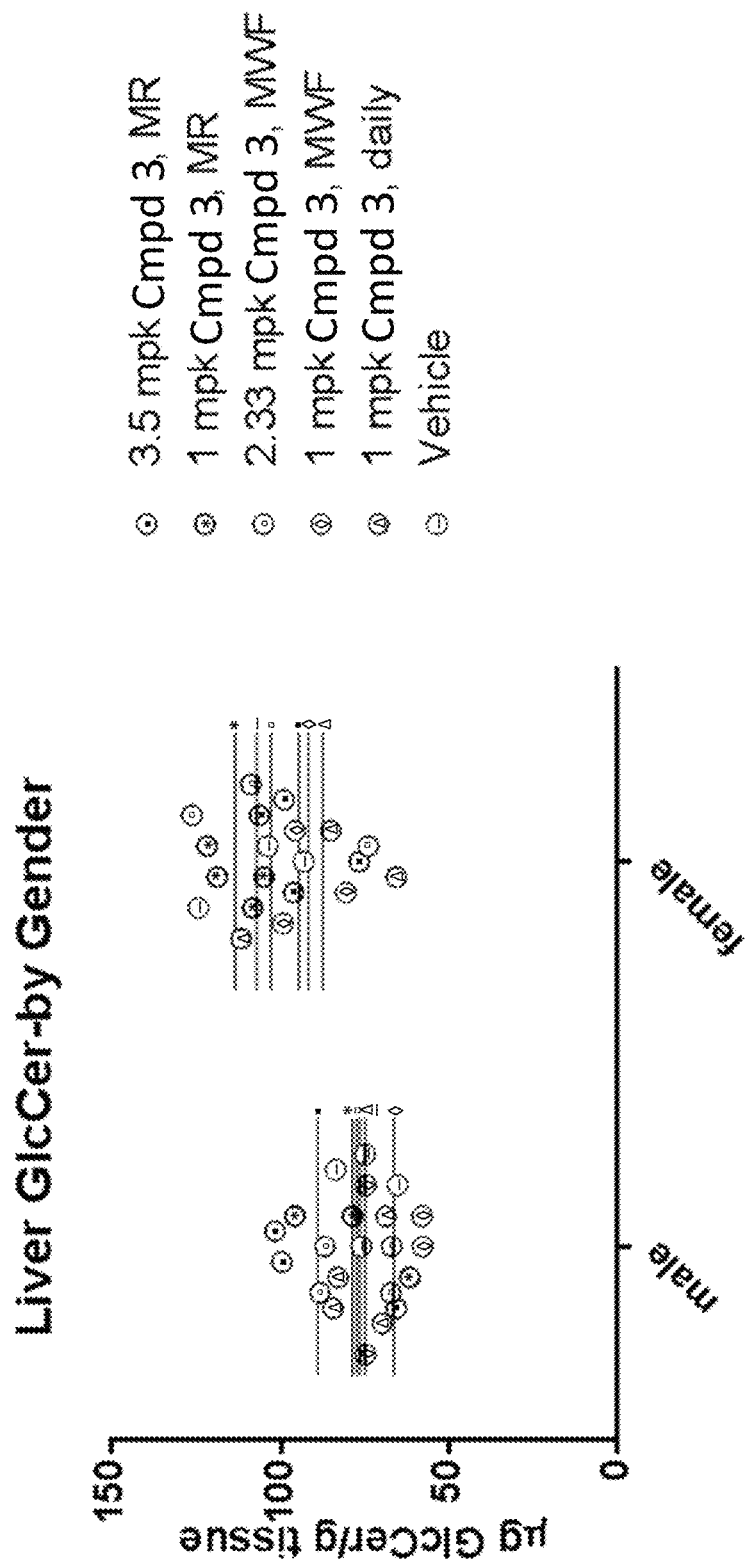
FIG. 19 shows gender differences in liver GlcCer levels of L444P mice after administration of (3R,4R,5S)-5-(difluoromethyl)piperidine-3,4-diol fumarate.

In FIG. 19, differences in gender were again explored. The only tissue affected by gender was the liver, in which the GlcCer concentration difference was significant. No gender effects for GlcCer were seen in the brain, spleen, or plasma. No gender effects were seen for GlcSph concentrations in the brain, liver, spleen, bone, or marrow. Additionally, no gender effects were seen with the measured activity of GCase enzyme in the brain, liver, or spleen. Ultimately, gender effects were only evident for liver weight in the 1 mg/kg FBE group, the brain in the 1 mg/kg FBE group, and the spleen weight in the vehicle group. No gender effects for total mouse weight seen at any time point.

Comparison of Examples 6-8

Changes in brain, liver, and spleen GCase activity were compared across the studies of Examples 6-8. In FIGS. 20 and 21, C1 denotes the study from Example 6, C2 denotes the study from Example 7, and C3 denotes the study from Example 8.

In FIG. 20, brain GCase activity was increased using the 0-10 mg/kg FBE ascending dose (this dose begins at 0.01 mg/kg FBE the first week, and increased by 10-fold each week. Thus, during the last week, mice are dosed with 10 mg/kg FBE) in both the studies of Examples 6 and 7. GCase activity in the brain was also increased after the 1 mg/kg FBE dose in both Example 7 and Example 8.

In the liver, the ascending dose showed higher GCase activity in both Example 6 and Example 7. GCase activity was also elevated in the 1 mg/kg FBE dosing regimens in Example 7 and Example 8.

Changes in GlcSph concentration were also compared across the three studies. In FIG. 21, the GlcSph substrate level change in the spleen was significant in the studies of Examples 6-8, with both the ascending dose (0-10 mg/kg FBE) and the 1 mg/kg FBE dose. In the brain, an increased level of GlcSph over the vehicle was seen in a dose of 10 mg/kg FBE, and in the ascending dose (0-10 mg/kg FBE).

What is claimed is:

1. A method for treating a patient having low β-glucocerebrosidase (GCase) activity, the method comprising:
   administering to the patient an effective amount of (3R, 4R,5S)-5-(difluoromethyl) piperidine-3,4-diol or a salt thereof to enhance the GCase activity in the patient, wherein the effective amount is in the range of about 0.75 mg/kg to about 2.5 mg/kg free base equivalent (FBE) per day and the effective amount is administered less than or equal to 7 days a week.

2. The method of claim 1, wherein the effective amount is in the range of about 0.75 mg/kg to about 1.5 mg/kg FBE per day.

3. The method of claim 1, wherein the (3R,4R,5S)-5-(difluoromethyl) piperidine-3,4-diol or salt thereof is administered 7 days a week.

4. The method of claim 1, wherein the (3R,4R,5S)-5-(difluoromethyl) piperidine-3,4-diol or salt thereof is administered orally.

5. The method of claim 1, wherein the salt is (3R,4R,5S)-5-(difluoromethyl)piperidine-3,4-diol fumarate.

6. The method of claim 1, wherein the (3R,4R,5S)-5-(difluoromethyl) piperidine-3,4-diol or salt thereof is administered about every 24 hours.

7. The method of claim 1, wherein the effective amount is about 1 mg/kg FBE per day.

8. The method of claim 1, wherein the effective amount is about 0.75 mg/kg to about 1 mg/kg FBE per day.

9. The method of claim 1, wherein the patient is diagnosed with Gaucher disease.

10. The method of claim 1, wherein the patient is diagnosed with Parkinson's disease.

11. A method for reducing glucosylsphingosine (GlcSph) in a patient having low β-glucocerebrosidase (GCase) activity, the method comprising:
    administering to the patient an effective amount of (3R,4R,5S)-5-(difluoromethyl) piperidine-3,4-diol or a salt thereof,
    wherein the effective amount is in the range of about 0.75 mg/kg to about 2.5 mg/kg free base equivalent (FBE) per day and the effective amount is administered less than or equal to 7 days a week.

12. The method of claim 11, wherein the salt is (3R,4R,5S)-5-(difluoromethyl)piperidine-3,4-diol fumarate.

13. The method of claim 11, wherein the (3R,4R,5S)-5-(difluoromethyl) piperidine-3,4-diol or salt thereof is administered orally.

14. The method of claim 11, wherein the effective amount is about 1 mg/kg FBE per day.

15. The method of claim 11, wherein the effective amount is in the range of about 0.75 to about 1.5 mg/kg FBE per day.

16. The method of claim 11, wherein the effective amount is about 0.75 mg/kg to about 1 mg/kg FBE per day.

17. The method of claim 11, wherein the (3R,4R,5S)-5-(difluoromethyl) piperidine-3,4-diol or salt thereof is administered 7 days a week.

18. The method of claim 11, wherein the (3R,4R,5S)-5-(difluoromethyl) piperidine-3,4-diol or salt thereof is administered about every 24 hours.

* * * * *